US012778507B2

(12) United States Patent
Huopana et al.

(10) Patent No.: US 12,778,507 B2
(45) Date of Patent: Nov. 3, 2026

(54) TECHNIQUES FOR MANUFACTURING A WEARABLE RING DEVICE WITH AN OUTER COVER CAPABLE OF ROTATION THROUGH COUPLING OF SIDE COVERS

(71) Applicant: Oura Health Oy, Oulu (FI)

(72) Inventors: Jouni Juhani Huopana, Oulu (FI); Antti Kalevi Lämsä, Oulu (FI)

(73) Assignee: Oura Health Oy, Oulu (FI)

( * ) Notice: Subject to any disclaimer, the term of this patent is extended or adjusted under 35 U.S.C. 154(b) by 265 days.

(21) Appl. No.: 18/476,001

(22) Filed: Sep. 27, 2023

(65) Prior Publication Data

US 2025/0099036 A1 Mar. 27, 2025

(51) Int. Cl.
*A61B 5/00* (2006.01)
*H02J 50/10* (2016.01)
*H02J 50/40* (2016.01)

(52) U.S. Cl.
CPC ............ *A61B 5/6826* (2013.01); *A61B 5/742* (2013.01); *A61B 2560/0219* (2013.01); *A61B 2560/0406* (2013.01); *H02J 50/10* (2016.02); *H02J 50/40* (2016.02)

(58) Field of Classification Search
None
See application file for complete search history.

(56) References Cited

U.S. PATENT DOCUMENTS 6,402,690 B1 * 6/2002 Rhee .................... A61B 5/0002 600/323
9,626,031 B2 * 4/2017 Dow ...................... G06V 40/12
10,156,867 B2 * 12/2018 von Badinski ......... G01P 15/00
10,568,525 B1 * 2/2020 Wu ...................... A61B 5/6824
11,714,494 B2 * 8/2023 D'Amone ............. G06F 3/0362 345/156
11,733,790 B2 * 8/2023 Beyhs ..................... G06F 3/016 345/184
12,216,829 B2 * 2/2025 Koskimäki .............. A61B 5/01
12,436,563 B2 * 10/2025 Vallius .................... G06F 1/163
2011/0007035 A1 * 1/2011 Shai ...................... G06F 3/0304 345/179
2016/0077582 A1 * 3/2016 Song ..................... G06F 3/0488 345/173
2016/0317060 A1 * 11/2016 Connor .................. G16H 20/60
(Continued)

FOREIGN PATENT DOCUMENTS

JP 2008206857 A * 9/2008

OTHER PUBLICATIONS

Clarivate analytics, machine translation of JP-2008206857-A (Year: 2025).*

*Primary Examiner* — Manolis Pahakis
(74) *Attorney, Agent, or Firm* — ArentFox Schiff LLP

(57) ABSTRACT

Methods, systems, and devices for manufacturing of a wearable ring device are described. Generally the techniques described herein may support manufacturing of a wearable ring device with an outer housing capable of rotation. For example, a wearable ring device may include an inner housing, one or more side covers, and an outer housing. The inner housing may be statically coupled, or fixed, to the one or more side covers, while the outer housing may be non-statically, or slidably, coupled to the one or more side covers, such that the outer housing may rotate around the inner housing while the inner housing remains stationary.

13 Claims, 11 Drawing Sheets

400

(56) References Cited

U.S. PATENT DOCUMENTS

| | | | | |
|---|---|---|---|---|
| 2018/0014782 | A1* | 1/2018 | Marcus | A61B 5/6843 |
| 2018/0211020 | A1* | 7/2018 | Fukuda | G06T 1/00 |
| 2021/0037932 | A1* | 2/2021 | Min | A61B 5/0006 |
| 2022/0233142 | A1* | 7/2022 | Hasan | A61B 5/681 |
| 2023/0072436 | A1* | 3/2023 | Sanchez | H02J 50/001 |
| 2023/0341944 | A1* | 10/2023 | Koskimäki | A61B 5/02405 |
| 2024/0249553 | A1* | 7/2024 | Branan | A61B 5/681 |
| 2024/0396371 | A1* | 11/2024 | Haverinen | A61B 5/6826 |
| 2025/0009084 | A1* | 1/2025 | Mäkinen | A44C 9/0053 |
| 2025/0009085 | A1* | 1/2025 | Mäkinen | A44C 9/0053 |
| 2025/0009086 | A1* | 1/2025 | Mäkinen | A44C 9/02 |
| 2025/0060780 | A1* | 2/2025 | Vallius | A61B 5/6826 |
| 2025/0099036 | A1* | 3/2025 | Huopana | A61B 5/6826 |
| 2025/0135689 | A1* | 5/2025 | Lämsä | B29C 41/20 |
| 2025/0278954 | A1* | 9/2025 | Branan | G06V 40/145 |

* cited by examiner

1100

TECHNIQUES FOR MANUFACTURING A WEARABLE RING DEVICE WITH AN OUTER COVER CAPABLE OF ROTATION THROUGH COUPLING OF SIDE COVERS

FIELD OF TECHNOLOGY

The following relates to wearable devices and data processing, including techniques for manufacturing a wearable ring device with an outer cover capable of rotation.

BACKGROUND

Some wearable devices may be configured to collect data from a user with reference to a measurement point on the user's finger to help the user understand more about their overall physiological health and well-being. However, wearable devices may be exposed to external forces while worn by the user that may cause the wearable devices to inadvertently rotate around the user's finger. Inadvertent rotation of the wearable ring device may result in a change of the measurement point used to collect physiological data without an awareness of the user, reducing accuracy of the collected physiological data.

DETAILED DESCRIPTION

Figure 1:
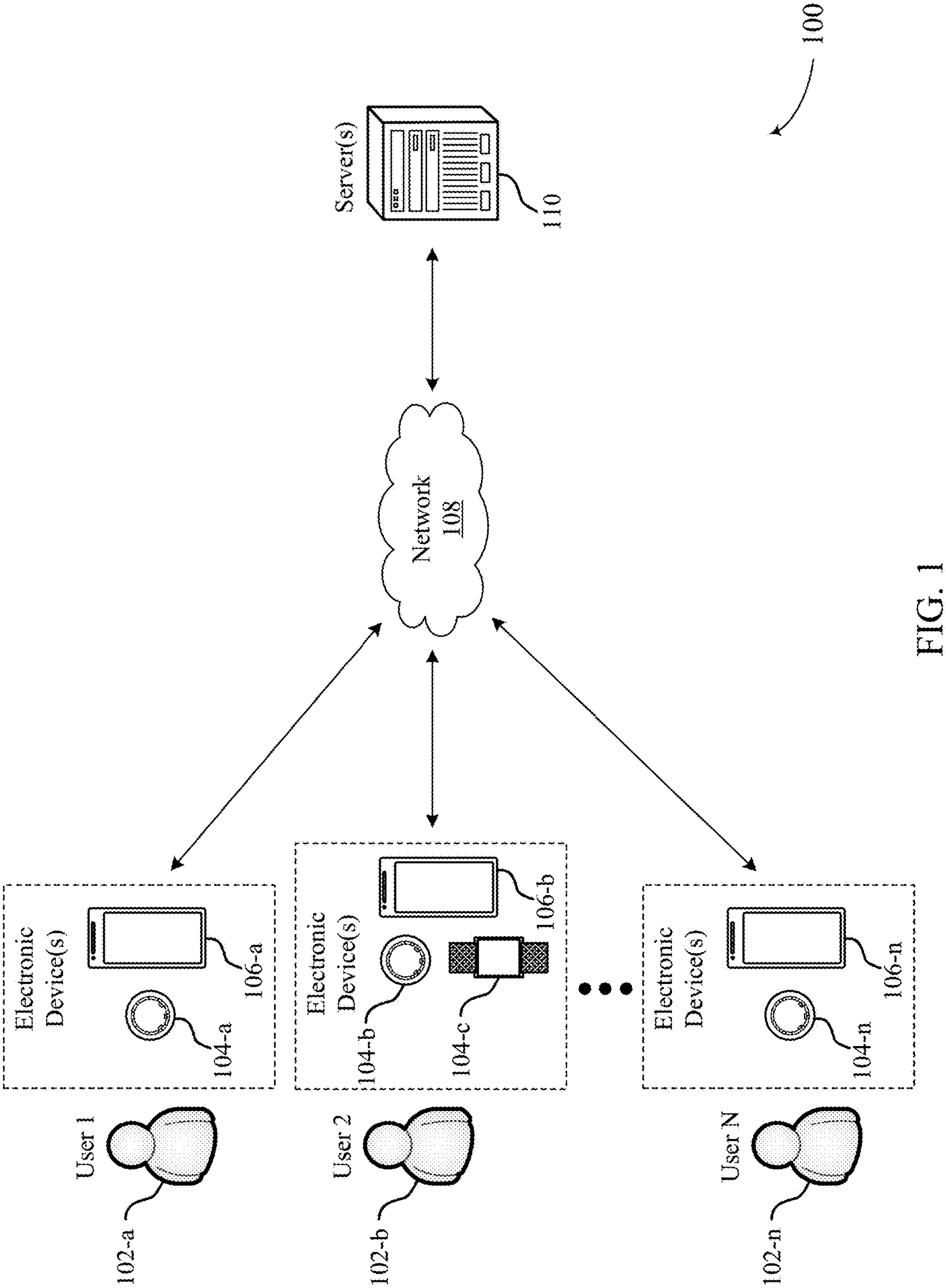
FIG. 1 illustrates an example of a system that supports techniques for manufacturing a wearable ring device with an outer cover capable of rotation in accordance with aspects of the present disclosure.

Some wearable ring devices may collect physiological data via one or more sensors (e.g., optical components) on the wearable ring device. In such cases, each sensor may collect the physiological data with reference to a measurement point on the user's finger. The term "measurement point" may refer to a radial position/location on the user's finger where a sensor performs physiological measurements. Due to the physiology of the human finger, the wearable ring device may achieve the best signal and highest quality data when the optical components are facing the palm-side of the finger. As such, rings may acquire the highest quality data using measurement points on the palm-side of the user's finger. However, in some cases, the wearable ring device may be inadvertently rotated around the user's finger due to an external force, resulting in a change of the measurement point used by each sensor to collect physiological data (e.g., each sensor may become rotated to measurement points on dorsal side of user's finger). However, the user and/or wearable ring device may be unaware that the wearable ring device was rotated and, as such, may interpret associated changes in collected physiological data as being based on a change in the user's physiology, rather than due to a change of optical measurement point, thereby reducing accuracy of the collected physiological data.

Accordingly, techniques described herein may support manufacturing of wearable ring devices to enable an outer cover of the wearable ring device to rotate relative to the rest of the wearable ring device. For example, electrical components (e.g., the printed circuit board (PCB) and one or more sensors) of the wearable ring device may be attached to an inner metal shell of the wearable ring device and the inner metal shell (e.g., and attached electrical components) may be placed into a mold, such that a clear epoxy may be injection molded to secure the electrical components to the inner metal shell. The injection molding may further fill one or more apertures of the inner metal shell with the clear epoxy, such that the one or more optical sensors may be secured with relation to the one or more apertures to enable data collection. The result of injection molding the inner metal shell to the electrical components may simply be referred to as an inner cover, or a ring engine assembly, that is essentially an operational ring without an outer cover.

Subsequently, an outer cover may be slid around the inner cover and may be secured to the inner cover in a non-static manner to finish the ring. For example, one or more side covers may be coupled to the inner cover in a fixed manner (e.g., statically coupled), while the outer cover may be coupled to the one or more side covers in a non-fixed, or slidable, manner (e.g., non-statically coupled). In such cases, the outer cover may be able to "slide" along the side covers to allow the outer cover to rotate relative to the inner cover, including the one or more sensors. As such, the outer cover may rotate around the inner cover (and the one or more sensors) under an applied force, such that the inner cover remains in a fixed position relative to the user's finger, and measurement points used by the one or more sensors do not change (e.g., remain the same) as the outer cover rotates. In some examples, the outer cover may rotate freely (e.g., un-restricted) around the inner cover while, in some other examples, the outer cover may rotate in a defined (e.g., restricted) range of motion, where the range of motion is limited based on one or more stopping components in the wearable ring device.

In some cases, other mechanical components, such as bearings (or bushings) may be used to enable the outer cover to rotate relative to the inner cover. As such, in cases where the wearable ring device is inadvertently bumped into an object (e.g., exposed to an external force), the outer cover may be configured to rotate in response to the external force, thereby preventing the entire wearable ring device from rotating, and enabling the measurement points to remain stationary (e.g., sensors stay facing the palm-side of the user's finger).

In some cases, the rotation of the outer cover relative to the inner cover may be harnessed for energy-harvesting purposes (e.g., to perform a wireless charging procedure). That is, the inner cover, the outer cover, or both, may include one or more wireless charging elements, such that rotation of the outer cover relative to the inner cover may generate an electrical signal via the wireless charging elements, where the electrical signal is used to charge a battery of the wearable ring device. For example, the outer cover and the inner cover may each include inductive charging elements, such as one or more magnets positioned at least partially within the outer cover and one or more coils positioned at least partially within the inner cover. The one or more magnets may be positioned relative to the one or more coils, such that rotation of the outer cover relative to the inner cover causes the magnets of the outer cover to induce an electrical current within the coils of the inner cover, where the electrical current charges the battery of the wearable ring device. In some examples, the wearable ring device may include one or more light emitting devices (LEDs) that emit light while the wearable ring device performs the wireless charging procedure.

Additionally, or alternatively, rotation of the outer cover relative to the inner cover may enable the user to input one or more ring-inputted commands via the rotation. For example, the wearable ring device may include one or more spring components that enables the outer cover of the wearable ring device to return to an initial, or reference, position after rotation. In such cases, the user may rotate the wearable ring device in a first rotational direction (e.g., clockwise) or a second rotational direction (e.g., counter-clockwise) and, upon completion of the rotation, the outer cover may return to the initial position. Additionally, the wearable ring device may include one or more additional sensors to identify when the outer cover is rotated in the first rotational direction and rotated in the second rotational direction. As such, a system associated with the wearable ring device may identify a sequence of rotations of the outer cover, where each rotation of the sequence of rotations is based on a rotational direction of the outer cover, and may match the sequence of rotations to a ring-inputted command. In other words, each ring-inputted command defined in the system may be associated with a configured "reference" sequence of rotations. As such, the system may compare an inputted sequence of rotations with a set of reference sequences associated with the ring-inputted commands to identify whether the input sequence of rotations matches one of the reference sequences. Thus, the system may perform the ring-inputted command associated with the identified reference sequence of rotations.

In some examples, a configured (e.g., reference) sequence of rotations associated with a ring-inputted command may be based on a magnitude of rotation of the outer cover, as well as the rotational direction of the outer cover, for each rotation of the sequence. That is, the one or more additional sensors may be configured to identify an end position of the outer cover following each rotation relative to the initial position of the outer cover prior to rotation. The system may identify a radial difference between each end position of the outer cover and the initial position of the outer cover for each rotation of the sequence. Thus, the user may input a sequence of rotations, where each rotation of the sequence of rotations may be associated with a magnitude of rotation of the outer cover (e.g., radial difference between end position and initial position) and a rotational direction of the outer cover. Additionally, each rotation of configured/reference sequences of rotations associated with the ring-inputted commands may similarly be associated with a magnitude of rotation of the outer and a rotational direction of the outer cover, such that the system may match the input sequence of rotations with a configured reference sequence of rotations based on the magnitude of rotation and the rotational direction of each rotation, and may perform the associated ring-inputted command.

Additionally, or alternatively, the wearable ring device may include one or more indexing components, such that the reference sequences associated with the ring-inputted commands may be based on an index associated with each rotation of the sequence. For example, the one or more indexing components may include one or more visual indexing components (e.g., lines, markers, etc.), one or more auditory indexing components (e.g., beeps, chimes, etc.), one or more tactile indexing components (e.g., vibrations, ridges, etc.), or any combination thereof, such that when the user rotates the outer cover, the user is able to identify an index associated with the rotation. As such, the one or more additional sensors may identify an index associated with each rotation of a sequence of rotations. Thus, the user may input a sequence of rotations, where each rotation of the sequence of rotations may be associated with an index. Additionally, each rotation of configured sequences of rotations associated with the ring-inputted commands may similarly be associated with an index, such that the system may match the input sequence of rotations with a reference sequence based on the indices, and may perform the ring-inputted command associated with the matched reference sequence.

Aspects of the disclosure are initially described in the context of systems supporting physiological data collection from users via wearable devices. Aspects of the disclosure are further illustrated in a cross-sectional view of a wearable ring device and command patterns. Aspects of the disclosure are further illustrated by and described with reference to apparatus diagrams, system diagrams, and flowcharts that relate to techniques for rotating an outer cover of a wearable ring device.

FIG. 1 illustrates an example of a system 100 that supports techniques for manufacturing a wearable ring device with an outer cover capable of rotation in accordance with aspects of the present disclosure. The system 100 includes a plurality of electronic devices (e.g., wearable devices 104, user devices 106) that may be worn and/or operated by one or more users 102. The system 100 further includes a network 108 and one or more servers 110.

The electronic devices may include any electronic devices known in the art, including wearable devices 104 (e.g., ring wearable devices, watch wearable devices, etc.), user devices 106 (e.g., smartphones, laptops, tablets). The electronic devices associated with the respective users 102 may include one or more of the following functionalities: 1) measuring physiological data, 2) storing the measured data, 3) processing the data, 4) providing outputs (e.g., via GUIs) to a user 102 based on the processed data, and 5) communicating data with one another and/or other computing devices. Different electronic devices may perform one or more of the functionalities.

Example wearable devices 104 may include wearable computing devices, such as a ring computing device (hereinafter "ring") configured to be worn on a user's 102 finger, a wrist computing device (e.g., a smart watch, fitness band, or bracelet) configured to be worn on a user's 102 wrist, and/or a head mounted computing device (e.g., glasses/goggles). Wearable devices 104 may also include bands, straps (e.g., flexible or inflexible bands or straps), stick-on sensors, and the like, that may be positioned in other locations, such as bands around the head (e.g., a forehead headband), arm (e.g., a forearm band and/or bicep band), and/or leg (e.g., a thigh or calf band), behind the ear, under the armpit, and the like. Wearable devices 104 may also be attached to, or included in, articles of clothing. For example, wearable devices 104 may be included in pockets and/or pouches on clothing. As another example, wearable device 104 may be clipped and/or pinned to clothing, or may otherwise be maintained within the vicinity of the user 102. Example articles of clothing may include, but are not limited to, hats, shirts, gloves, pants, socks, outerwear (e.g., jackets), and undergarments. In some implementations, wearable devices 104 may be included with other types of devices such as training/sporting devices that are used during physical activity. For example, wearable devices 104 may be attached to, or included in, a bicycle, skis, a tennis racket, a golf club, and/or training weights.

Much of the present disclosure may be described in the context of a ring wearable device 104. Accordingly, the terms "ring 104," "wearable device 104," and like terms, may be used interchangeably, unless noted otherwise herein. However, the use of the term "ring 104" is not to be regarded as limiting, as it is contemplated herein that aspects of the present disclosure may be performed using other wearable devices (e.g., watch wearable devices, necklace wearable device, bracelet wearable devices, earring wearable devices, anklet wearable devices, and the like).

In some aspects, user devices 106 may include handheld mobile computing devices, such as smartphones and tablet computing devices. User devices 106 may also include personal computers, such as laptop and desktop computing devices. Other example user devices 106 may include server computing devices that may communicate with other electronic devices (e.g., via the Internet). In some implementations, computing devices may include medical devices, such as external wearable computing devices (e.g., Holter monitors). Medical devices may also include implantable medical devices, such as pacemakers and cardioverter defibrillators. Other example user devices 106 may include home computing devices, such as internet of things (IoT) devices (e.g., IoT devices), smart televisions, smart speakers, smart displays (e.g., video call displays), hubs (e.g., wireless communication hubs), security systems, smart appliances (e.g., thermostats and refrigerators), and fitness equipment.

Some electronic devices (e.g., wearable devices 104, user devices 106) may measure physiological parameters of respective users 102, such as photoplethysmography waveforms, continuous skin temperature, a pulse waveform, respiration rate, heart rate, heart rate variability (HRV), actigraphy, galvanic skin response, pulse oximetry, blood oxygen saturation (SpO2), blood sugar levels (e.g., glucose metrics), and/or other physiological parameters. Some electronic devices that measure physiological parameters may also perform some/all of the calculations described herein. Some electronic devices may not measure physiological parameters, but may perform some/all of the calculations described herein. For example, a ring (e.g., wearable device 104), mobile device application, or a server computing device may process received physiological data that was measured by other devices.

In some implementations, a user 102 may operate, or may be associated with, multiple electronic devices, some of which may measure physiological parameters and some of which may process the measured physiological parameters. In some implementations, a user 102 may have a ring (e.g., wearable device 104) that measures physiological parameters. The user 102 may also have, or be associated with, a user device 106 (e.g., mobile device, smartphone), where the wearable device 104 and the user device 106 are communicatively coupled to one another. In some cases, the user device 106 may receive data from the wearable device 104 and perform some/all of the calculations described herein. In some implementations, the user device 106 may also measure physiological parameters described herein, such as motion/activity parameters.

For example, as illustrated in FIG. 1, a first user 102-*a* (User 1) may operate, or may be associated with, a wearable device 104-*a* (e.g., ring 104-*a*) and a user device 106-*a* that may operate as described herein. In this example, the user device 106-*a* associated with user 102-*a* may process/store physiological parameters measured by the ring 104-*a*. Comparatively, a second user 102-*b* (User 2) may be associated with a ring 104-*b*, a watch wearable device 104-*c* (e.g., watch 104-*c*), and a user device 106-*b*, where the user device 106-*b* associated with user 102-*b* may process/store physiological parameters measured by the ring 104-*b* and/or the watch 104-*c*. Moreover, an nth user 102-*n* (User N) may be associated with an arrangement of electronic devices described herein (e.g., ring 104-*n*, user device 106-*n*). In some aspects, wearable devices 104 (e.g., rings 104, watches 104) and other electronic devices may be communicatively coupled to the user devices 106 of the respective users 102 via Bluetooth, Wi-Fi, and other wireless protocols.

In some implementations, the rings 104 (e.g., wearable devices 104) of the system 100 may be configured to collect physiological data from the respective users 102 based on arterial blood flow within the user's finger. In particular, a ring 104 may utilize one or more light-emitting components, such as LEDs (e.g., red LEDs, green LEDs) that emit light on the palm-side of a user's finger to collect physiological data based on arterial blood flow within the user's finger. In general, the terms light-emitting components, light-emitting elements, and like terms, may include, but are not limited to, LEDs, micro LEDs, mini LEDs, laser diodes (LDs) (e.g., vertical cavity surface-emitting lasers (VCSELs), and the like.

In some cases, the system 100 may be configured to collect physiological data from the respective users 102 based on blood flow diffused into a microvascular bed of skin with capillaries and arterioles. For example, the system 100 may collect PPG data based on a measured amount of blood diffused into the microvascular system of capillaries and arterioles. In some implementations, the ring 104 may acquire the physiological data using a combination of both green and red LEDs. The physiological data may include any physiological data known in the art including, but not limited to, temperature data, accelerometer data (e.g., movement/motion data), heart rate data, HRV data, blood oxygen level data, or any combination thereof.

The use of both green and red LEDs may provide several advantages over other solutions, as red and green LEDs have been found to have their own distinct advantages when acquiring physiological data under different conditions (e.g., light/dark, active/inactive) and via different parts of the body, and the like. For example, green LEDs have been found to exhibit better performance during exercise. Moreover, using multiple LEDs (e.g., green and red LEDs) distributed around the ring 104 has been found to exhibit superior performance as compared to wearable devices that utilize LEDs that are positioned close to one another, such as within a watch wearable device. Furthermore, the blood vessels in the finger (e.g., arteries, capillaries) are more accessible via LEDs as compared to blood vessels in the wrist. In particular, arteries in the wrist are positioned on the bottom of the wrist (e.g., palm-side of the wrist), meaning only capillaries are accessible on the top of the wrist (e.g., back of hand side of the wrist), where wearable watch devices and similar devices are typically worn. As such, utilizing LEDs and other sensors within a ring 104 has been found to exhibit superior performance as compared to wearable devices worn on the wrist, as the ring 104 may have greater access to arteries (as compared to capillaries), thereby resulting in stronger signals and more valuable physiological data.

The electronic devices of the system 100 (e.g., user devices 106, wearable devices 104) may be communicatively coupled to one or more servers 110 via wired or wireless communication protocols. For example, as shown in FIG. 1, the electronic devices (e.g., user devices 106) may be communicatively coupled to one or more servers 110 via a network 108. The network 108 may implement transfer control protocol and internet protocol (TCP/IP), such as the Internet, or may implement other network 108 protocols. Network connections between the network 108 and the respective electronic devices may facilitate transport of data via email, web, text messages, mail, or any other appropriate form of interaction within a computer network 108. For example, in some implementations, the ring 104-*a* associated with the first user 102-*a* may be communicatively coupled to the user device 106-*a*, where the user device 106-*a* is communicatively coupled to the servers 110 via the network 108. In additional or alternative cases, wearable devices 104 (e.g., rings 104, watches 104) may be directly communicatively coupled to the network 108.

The system 100 may offer an on-demand database service between the user devices 106 and the one or more servers 110. In some cases, the servers 110 may receive data from the user devices 106 via the network 108, and may store and analyze the data. Similarly, the servers 110 may provide data to the user devices 106 via the network 108. In some cases, the servers 110 may be located at one or more data centers. The servers 110 may be used for data storage, management, and processing. In some implementations, the servers 110 may provide a web-based interface to the user device 106 via web browsers.

In some aspects, the system 100 may detect periods of time that a user 102 is asleep, and classify periods of time that the user 102 is asleep into one or more sleep stages (e.g., sleep stage classification). For example, as shown in FIG. 1, User 102-*a* may be associated with a wearable device 104-*a* (e.g., ring 104-*a*) and a user device 106-*a*. In this example, the ring 104-*a* may collect physiological data associated with the user 102-*a*, including temperature, heart rate, HRV, respiratory rate, and the like. In some aspects, data collected by the ring 104-*a* may be input to a machine learning classifier, where the machine learning classifier is configured to determine periods of time that the user 102-*a* is (or was) asleep. Moreover, the machine learning classifier may be configured to classify periods of time into different sleep stages, including an awake sleep stage, a rapid eye movement (REM) sleep stage, a light sleep stage (non-REM (NREM)), and a deep sleep stage (NREM). In some aspects, the classified sleep stages may be displayed to the user 102-*a* via a GUI of the user device 106-*a*. Sleep stage classification may be used to provide feedback to a user 102-*a* regarding the user's sleeping patterns, such as recommended bedtimes, recommended wake-up times, and the like. Moreover, in some implementations, sleep stage classification techniques described herein may be used to calculate scores for the respective user, such as Sleep Scores, Readiness Scores, and the like.

In some aspects, the system 100 may utilize circadian rhythm-derived features to further improve physiological data collection, data processing procedures, and other techniques described herein. The term circadian rhythm may refer to a natural, internal process that regulates an individual's sleep-wake cycle, that repeats approximately every 24 hours. In this regard, techniques described herein may utilize circadian rhythm adjustment models to improve physiological data collection, analysis, and data processing. For example, a circadian rhythm adjustment model may be input into a machine learning classifier along with physiological data collected from the user 102-*a* via the wearable device 104-*a*. In this example, the circadian rhythm adjustment model may be configured to "weight," or adjust, physiological data collected throughout a user's natural, approximately 24-hour circadian rhythm. In some implementations, the system may initially start with a "baseline" circadian rhythm adjustment model, and may modify the baseline model using physiological data collected from each user 102 to generate tailored, individualized circadian rhythm adjustment models that are specific to each respective user 102.

In some aspects, the system 100 may utilize other biological rhythms to further improve physiological data collection, analysis, and processing by phase of these other rhythms. For example, if a weekly rhythm is detected within an individual's baseline data, then the model may be configured to adjust "weights" of data by day of the week. Biological rhythms that may require adjustment to the model by this method include: 1) ultradian (faster than a day rhythms, including sleep cycles in a sleep state, and oscillations from less than an hour to several hours periodicity in the measured physiological variables during wake state; 2) circadian rhythms; 3) non-endogenous daily rhythms shown to be imposed on top of circadian rhythms, as in work schedules; 4) weekly rhythms, or other artificial time periodicities exogenously imposed (e.g. in a hypothetical culture with 12 day "weeks," 12 day rhythms could be used); 5) multi-day ovarian rhythms in women and spermatogenesis rhythms in men; 6) lunar rhythms (relevant for individuals living with low or no artificial lights); and 7) seasonal rhythms.

The biological rhythms are not always stationary rhythms. For example, many women experience variability in ovarian cycle length across cycles, and ultradian rhythms are not expected to occur at exactly the same time or periodicity across days even within a user. As such, signal processing techniques sufficient to quantify the frequency composition while preserving temporal resolution of these rhythms in physiological data may be used to improve detection of these rhythms, to assign phase of each rhythm to each moment in time measured, and to thereby modify adjustment models and comparisons of time intervals. The biological rhythm-adjustment models and parameters can be added in linear or non-linear combinations as appropriate to more accurately capture the dynamic physiological baselines of an individual or group of individuals.

In some aspects, the system 100 may include rings 104 manufactured with an outer cover that is capable of rotating around an inner cover of the ring 104. For example, a set of side covers may be coupled to the inner cover in a fixed manner (e.g., statically coupled), while the outer cover may be coupled to the inner cover in a non-fixed, or slidable, manner (e.g., non-statically coupled). In such cases, the outer cover may be able to "slide" along the side covers to allow the outer cover to freely rotate relative to the inner cover, including the one or more sensors. As such, the outer cover may rotate around the inner cover, and the one or more sensors, under an applied force, such that the inner cover remains in a fixed position relative to a finger of a user 102, and measurement points used by the one or more sensors do not change (e.g., remain the same) as the outer cover rotates. In some examples, the outer cover may rotate freely (e.g., un-restricted) around the inner cover while, in some other examples, the outer cover may rotate in a defined (e.g., restricted) range of motion, where the range of motion is limited based on one or more stopping components in the wearable ring device.

In some cases, other mechanical components, such as bearings (or bushings) may be used to enable the outer cover to rotate relative to the inner cover. As such, in cases where the ring 104 is inadvertently bumped into an object (e.g., exposed to an external force), the outer cover may be configured to rotate in response to the external force, thereby preventing the entire ring 104 from rotating, and enabling the measurement points to remain stationary (e.g., sensors stay facing the palm-side of the finger of the user 102), or otherwise reduce rotation of the ring.

It should be appreciated by a person skilled in the art that one or more aspects of the disclosure may be implemented in a system 100 to additionally or alternatively solve other problems than those described above. Furthermore, aspects of the disclosure may provide technical improvements to "conventional" systems or processes as described herein. However, the description and appended drawings only include example technical improvements resulting from implementing aspects of the disclosure, and accordingly do not represent all of the technical improvements provided within the scope of the claims.

Figure 2:
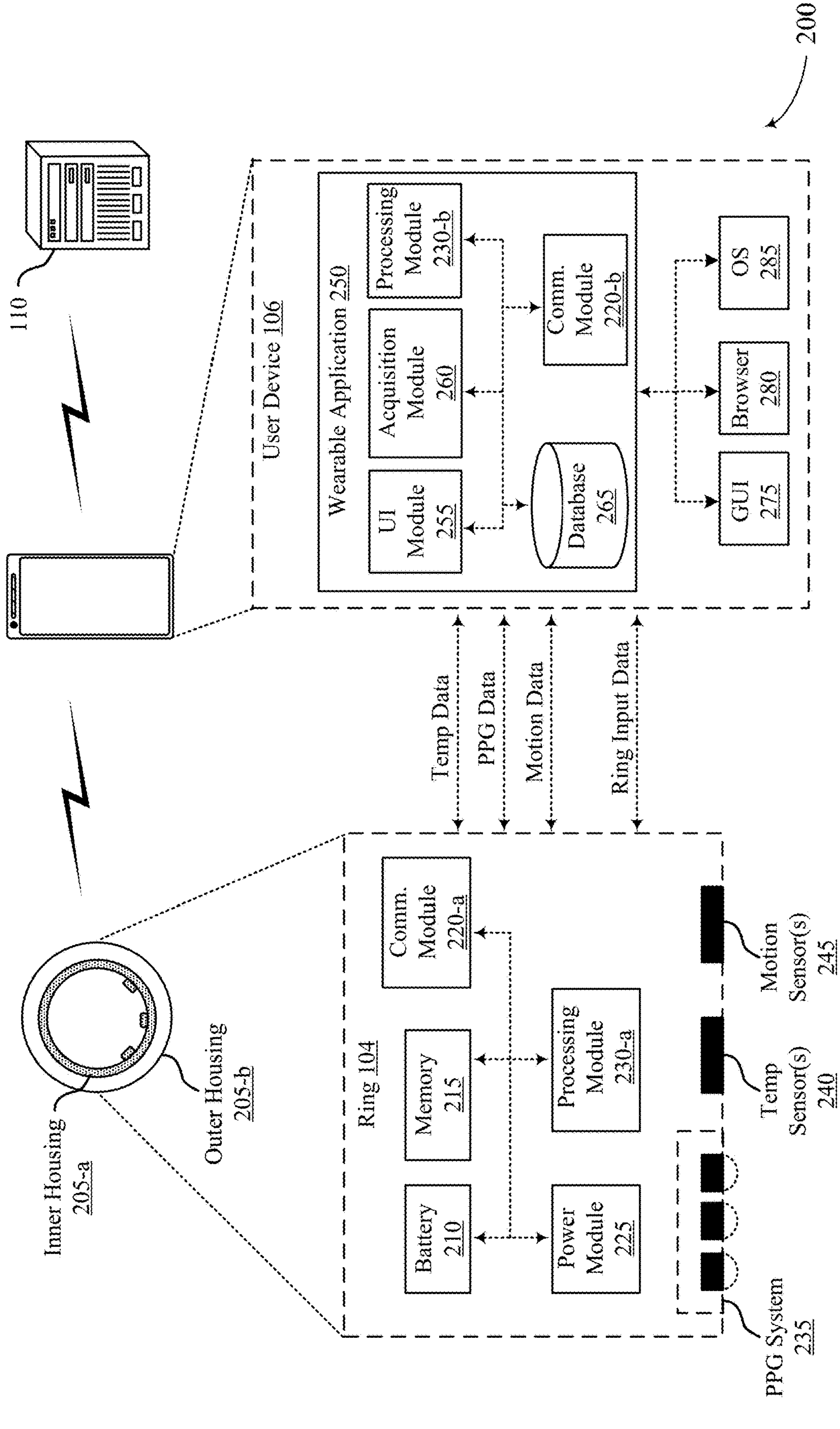
FIG. 2 illustrates an example of a system that supports techniques for manufacturing a wearable ring device with an outer cover capable of rotation in accordance with aspects of the present disclosure.

FIG. 2 illustrates an example of a system 200 that supports techniques for manufacturing a wearable ring device with an outer cover capable of rotation in accordance with aspects of the present disclosure. The system 200 may implement, or be implemented by, system 100. In particular, system 200 illustrates an example of a ring 104 (e.g., wearable device 104), a user device 106, and a server 110, as described with reference to FIG. 1.

In some aspects, the ring 104 may be configured to be worn around a user's finger, and may determine one or more user physiological parameters when worn around the user's finger. Example measurements and determinations may include, but are not limited to, user skin temperature, pulse waveforms, respiratory rate, heart rate, HRV, blood oxygen levels (SpO2), blood sugar levels (e.g., glucose metrics), and the like.

The system 200 further includes a user device 106 (e.g., a smartphone) in communication with the ring 104. For example, the ring 104 may be in wireless and/or wired communication with the user device 106. In some implementations, the ring 104 may send measured and processed data (e.g., temperature data, photoplethysmogram (PPG) data, motion/accelerometer data, ring input data, and the like) to the user device 106. The user device 106 may also send data to the ring 104, such as ring 104 firmware/configuration updates. The user device 106 may process data. In some implementations, the user device 106 may transmit data to the server 110 for processing and/or storage.

The ring 104 may include a housing 205 that may include an inner housing 205-*a* and an outer housing 205-*b*. In some aspects, the housing 205 of the ring 104 may store or otherwise include various components of the ring including, but not limited to, device electronics, a power source (e.g., battery 210, and/or capacitor), one or more substrates (e.g., printable circuit boards) that interconnect the device electronics and/or power source, and the like. The device electronics may include device modules (e.g., hardware/software), such as: a processing module 230-*a*, a memory 215, a communication module 220-*a*, a power module 225, and the like. The device electronics may also include one or more sensors. Example sensors may include one or more temperature sensors 240, a PPG sensor assembly (e.g., PPG system 235), and one or more motion sensors 245.

The sensors may include associated modules (not illustrated) configured to communicate with the respective components/modules of the ring 104, and generate signals associated with the respective sensors. In some aspects, each of the components/modules of the ring 104 may be communicatively coupled to one another via wired or wireless connections. Moreover, the ring 104 may include additional and/or alternative sensors or other components that are configured to collect physiological data from the user, including light sensors (e.g., LEDs), oximeters, and the like.

The ring 104 shown and described with reference to FIG. 2 is provided solely for illustrative purposes. As such, the ring 104 may include additional or alternative components as those illustrated in FIG. 2. Other rings 104 that provide functionality described herein may be fabricated. For example, rings 104 with fewer components (e.g., sensors) may be fabricated. In a specific example, a ring 104 with a single temperature sensor 240 (or other sensor), a power source, and device electronics configured to read the single temperature sensor 240 (or other sensor) may be fabricated. In another specific example, a temperature sensor 240 (or other sensor) may be attached to a user's finger (e.g., using adhesives, wraps, clamps, spring loaded clamps, etc.). In this case, the sensor may be wired to another computing device, such as a wrist worn computing device that reads the temperature sensor 240 (or other sensor). In other examples, a ring 104 that includes additional sensors and processing functionality may be fabricated.

The housing 205 may include one or more housing 205 components. The housing 205 may include an outer housing 205-*b* component (e.g., a shell) and an inner housing 205-*a* component (e.g., a molding). The housing 205 may include additional components (e.g., additional layers) not explicitly illustrated in FIG. 2. For example, in some implementations, the ring 104 may include one or more insulating layers that electrically insulate the device electronics and other conductive materials (e.g., electrical traces) from the outer housing 205-*b* (e.g., a metal outer housing 205-*b*). The housing 205 may provide structural support for the device electronics, battery 210, substrate(s), and other components. For example, the housing 205 may protect the device electronics, battery 210, and substrate(s) from mechanical forces, such as pressure and impacts. The housing 205 may also protect the device electronics, battery 210, and substrate(s) from water and/or other chemicals.

The outer housing 205-*b* may be fabricated from one or more materials. In some implementations, the outer housing 205-*b* may include a metal, such as titanium, that may provide strength and abrasion resistance at a relatively light weight. The outer housing 205-*b* may also be fabricated from other materials, such polymers. In some implementations, the outer housing 205-*b* may be protective as well as decorative.

The inner housing 205-*a* may be configured to interface with the user's finger. The inner housing 205-*a* may be formed from a polymer (e.g., a medical grade polymer) or other material. In some implementations, the inner housing 205-*a* may be transparent. For example, the inner housing 205-*a* may be transparent to light emitted by the PPG light emitting diodes (LEDs). In some implementations, the inner housing 205-*a* component may be molded onto the outer housing 205-*b*. For example, the inner housing 205-*a* may include a polymer that is molded (e.g., injection molded) to fit into an outer housing 205-*b* metallic shell.

The ring 104 may include one or more substrates (not illustrated). The device electronics and battery 210 may be included on the one or more substrates. For example, the device electronics and battery 210 may be mounted on one or more substrates. Example substrates may include one or more printed circuit boards (PCBs), such as flexible PCB (e.g., polyimide). In some implementations, the electronics/battery 210 may include surface mounted devices (e.g., surface-mount technology (SMT) devices) on a flexible PCB. In some implementations, the one or more substrates (e.g., one or more flexible PCBs) may include electrical traces that provide electrical communication between device electronics. The electrical traces may also connect the battery 210 to the device electronics.

The device electronics, battery 210, and substrates may be arranged in the ring 104 in a variety of ways. In some implementations, one substrate that includes device electronics may be mounted along the bottom of the ring 104 (e.g., the bottom half), such that the sensors (e.g., PPG system 235, temperature sensors 240, motion sensors 245, and other sensors) interface with the underside of the user's finger. In these implementations, the battery 210 may be included along the top portion of the ring 104 (e.g., on another substrate).

The various components/modules of the ring 104 represent functionality (e.g., circuits and other components) that may be included in the ring 104. Modules may include any discrete and/or integrated electronic circuit components that implement analog and/or digital circuits capable of producing the functions attributed to the modules herein. For example, the modules may include analog circuits (e.g., amplification circuits, filtering circuits, analog/digital conversion circuits, and/or other signal conditioning circuits). The modules may also include digital circuits (e.g., combinational or sequential logic circuits, memory circuits etc.).

The memory 215 (memory module) of the ring 104 may include any volatile, non-volatile, magnetic, or electrical media, such as a random access memory (RAM), read-only memory (ROM), non-volatile RAM (NVRAM), electrically-erasable programmable ROM (EEPROM), flash memory, or any other memory device. The memory 215 may store any of the data described herein. For example, the memory 215 may be configured to store data (e.g., motion data, temperature data, PPG data) collected by the respective sensors and PPG system 235. Furthermore, memory 215 may include instructions that, when executed by one or more processing circuits, cause the modules to perform various functions attributed to the modules herein. The device electronics of the ring 104 described herein are only example device electronics. As such, the types of electronic components used to implement the device electronics may vary based on design considerations.

The functions attributed to the modules of the ring 104 described herein may be embodied as one or more processors, hardware, firmware, software, or any combination thereof. Depiction of different features as modules is intended to highlight different functional aspects and does not necessarily imply that such modules must be realized by separate hardware/software components. Rather, functionality associated with one or more modules may be performed by separate hardware/software components or integrated within common hardware/software components.

The processing module 230-*a* of the ring 104 may include one or more processors (e.g., processing units), microcontrollers, digital signal processors, systems on a chip (SOCs), and/or other processing devices. The processing module 230-*a* communicates with the modules included in the ring 104. For example, the processing module 230-*a* may transmit/receive data to/from the modules and other components of the ring 104, such as the sensors. As described herein, the modules may be implemented by various circuit components. Accordingly, the modules may also be referred to as circuits (e.g., a communication circuit and power circuit).

The processing module 230-*a* may communicate with the memory 215. The memory 215 may include computer-readable instructions that, when executed by the processing module 230-*a*, cause the processing module 230-*a* to perform the various functions attributed to the processing module 230-*a* herein. In some implementations, the processing module 230-*a* (e.g., a microcontroller) may include additional features associated with other modules, such as communication functionality provided by the communication module 220-*a* (e.g., an integrated Bluetooth Low Energy transceiver) and/or additional onboard memory 215.

The communication module 220-*a* may include circuits that provide wireless and/or wired communication with the user device 106 (e.g., communication module 220-*b* of the user device 106). In some implementations, the communication modules 220-*a*, 220-*b* may include wireless communication circuits, such as Bluetooth circuits and/or Wi-Fi circuits. In some implementations, the communication modules 220-*a*, 220-*b* can include wired communication circuits, such as Universal Serial Bus (USB) communication circuits. Using the communication module 220-*a*, the ring 104 and the user device 106 may be configured to communicate with each other. The processing module 230-*a* of the ring may be configured to transmit/receive data to/from the user device 106 via the communication module 220-*a*. Example data may include, but is not limited to, motion data, temperature data, pulse waveforms, heart rate data, HRV data, PPG data, and status updates (e.g., charging status, battery charge level, and/or ring 104 configuration settings). The processing module 230-*a* of the ring may also be configured to receive updates (e.g., software/firmware updates) and data from the user device 106.

The ring 104 may include a battery 210 (e.g., a rechargeable battery 210). An example battery 210 may include a Lithium-Ion or Lithium-Polymer type battery 210, although a variety of battery 210 options are possible. The battery 210 may be wirelessly charged. In some implementations, the ring 104 may include a power source other than the battery 210, such as a capacitor. The power source (e.g., battery 210 or capacitor) may have a curved geometry that matches the curve of the ring 104. In some aspects, a charger or other power source may include additional sensors that may be used to collect data in addition to, or that supplements, data collected by the ring 104 itself. Moreover, a charger or other power source for the ring 104 may function as a user device 106, in which case the charger or other power source for the ring 104 may be configured to receive data from the ring 104, store and/or process data received from the ring 104, and communicate data between the ring 104 and the servers 110.

In some aspects, the ring 104 includes a power module 225 that may control charging of the battery 210. For example, the power module 225 may interface with an external wireless charger that charges the battery 210 when interfaced with the ring 104. The charger may include a datum structure that mates with a ring 104 datum structure to create a specified orientation with the ring 104 during charging. The power module 225 may also regulate voltage(s) of the device electronics, regulate power output to the device electronics, and monitor the state of charge of the battery 210. In some implementations, the battery 210 may include a protection circuit module (PCM) that protects the battery 210 from high current discharge, over voltage during charging, and under voltage during discharge. The power module 225 may also include electro-static discharge (ESD) protection.

The one or more temperature sensors 240 may be electrically coupled to the processing module 230-*a*. The temperature sensor 240 may be configured to generate a temperature signal (e.g., temperature data) that indicates a temperature read or sensed by the temperature sensor 240. The processing module 230-*a* may determine a temperature of the user in the location of the temperature sensor 240. For example, in the ring 104, temperature data generated by the temperature sensor 240 may indicate a temperature of a user at the user's finger (e.g., skin temperature). In some implementations, the temperature sensor 240 may contact the user's skin. In other implementations, a portion of the housing 205 (e.g., the inner housing 205-*a*) may form a barrier (e.g., a thin, thermally conductive barrier) between the temperature sensor 240 and the user's skin. In some implementations, portions of the ring 104 configured to contact the user's finger may have thermally conductive portions and thermally insulative portions. The thermally conductive portions may conduct heat from the user's finger to the temperature sensors 240. The thermally insulative portions may insulate portions of the ring 104 (e.g., the temperature sensor 240) from ambient temperature.

In some implementations, the temperature sensor 240 may generate a digital signal (e.g., temperature data) that the processing module 230-*a* may use to determine the temperature. As another example, in cases where the temperature sensor 240 includes a passive sensor, the processing module 230-*a* (or a temperature sensor 240 module) may measure a current/voltage generated by the temperature sensor 240 and determine the temperature based on the measured current/voltage. Example temperature sensors 240 may include a thermistor, such as a negative temperature coefficient (NTC) thermistor, or other types of sensors including resistors, transistors, diodes, and/or other electrical/electronic components.

The processing module 230-*a* may sample the user's temperature over time. For example, the processing module 230-*a* may sample the user's temperature according to a sampling rate. An example sampling rate may include one sample per second, although the processing module 230-*a* may be configured to sample the temperature signal at other sampling rates that are higher or lower than one sample per second. In some implementations, the processing module 230-*a* may sample the user's temperature continuously throughout the day and night. Sampling at a sufficient rate (e.g., one sample per second) throughout the day may provide sufficient temperature data for analysis described herein.

The processing module 230-*a* may store the sampled temperature data in memory 215. In some implementations, the processing module 230-*a* may process the sampled temperature data. For example, the processing module 230-*a* may determine average temperature values over a period of time. In one example, the processing module 230-*a* may determine an average temperature value each minute by summing all temperature values collected over the minute and dividing by the number of samples over the minute. In a specific example where the temperature is sampled at one sample per second, the average temperature may be a sum of all sampled temperatures for one minute divided by sixty seconds. The memory 215 may store the average temperature values over time. In some implementations, the memory 215 may store average temperatures (e.g., one per minute) instead of sampled temperatures in order to conserve memory 215.

The sampling rate, which may be stored in memory 215, may be configurable. In some implementations, the sampling rate may be the same throughout the day and night. In other implementations, the sampling rate may be changed throughout the day/night. In some implementations, the ring 104 may filter/reject temperature readings, such as large spikes in temperature that are not indicative of physiological changes (e.g., a temperature spike from a hot shower). In some implementations, the ring 104 may filter/reject temperature readings that may not be reliable due to other factors, such as excessive motion during exercise (e.g., as indicated by a motion sensor 245).

The ring 104 (e.g., communication module) may transmit the sampled and/or average temperature data to the user device 106 for storage and/or further processing. The user device 106 may transfer the sampled and/or average temperature data to the server 110 for storage and/or further processing.

Although the ring 104 is illustrated as including a single temperature sensor 240, the ring 104 may include multiple temperature sensors 240 in one or more locations, such as arranged along the inner housing 205-*a* near the user's finger. In some implementations, the temperature sensors 240 may be stand-alone temperature sensors 240. Additionally, or alternatively, one or more temperature sensors 240 may be included with other components (e.g., packaged with other components), such as with the accelerometer and/or processor.

The processing module 230-*a* may acquire and process data from multiple temperature sensors 240 in a similar manner described with respect to a single temperature sensor 240. For example, the processing module 230 may individually sample, average, and store temperature data from each of the multiple temperature sensors 240. In other examples, the processing module 230-*a* may sample the sensors at different rates and average/store different values for the different sensors. In some implementations, the processing module 230-*a* may be configured to determine a single temperature based on the average of two or more temperatures determined by two or more temperature sensors 240 in different locations on the finger.

The temperature sensors 240 on the ring 104 may acquire distal temperatures at the user's finger (e.g., any finger). For example, one or more temperature sensors 240 on the ring 104 may acquire a user's temperature from the underside of a finger or at a different location on the finger. In some implementations, the ring 104 may continuously acquire distal temperature (e.g., at a sampling rate). Although distal temperature measured by a ring 104 at the finger is described herein, other devices may measure temperature at the same/different locations. In some cases, the distal temperature measured at a user's finger may differ from the temperature measured at a user's wrist or other external body location.

Additionally, the distal temperature measured at a user's finger (e.g., a "shell" temperature) may differ from the user's core temperature. As such, the ring 104 may provide a useful temperature signal that may not be acquired at other internal/external locations of the body. In some cases, continuous temperature measurement at the finger may capture temperature fluctuations (e.g., small or large fluctuations) that may not be evident in core temperature. For example, continuous temperature measurement at the finger may capture minute-to-minute or hour-to-hour temperature fluctuations that provide additional insight that may not be provided by other temperature measurements elsewhere in the body.

The ring 104 may include a PPG system 235. The PPG system 235 may include one or more optical transmitters that transmit light. The PPG system 235 may also include one or more optical receivers that receive light transmitted by the one or more optical transmitters. An optical receiver may generate a signal (hereinafter "PPG" signal) that indicates an amount of light received by the optical receiver. The optical transmitters may illuminate a region of the user's finger. The PPG signal generated by the PPG system 235 may indicate the perfusion of blood in the illuminated region. For example, the PPG signal may indicate blood volume changes in the illuminated region caused by a user's pulse pressure. The processing module 230-*a* may sample the PPG signal and determine a user's pulse waveform based on the PPG signal. The processing module 230-*a* may determine a variety of physiological parameters based on the user's pulse waveform, such as a user's respiratory rate, heart rate, HRV, oxygen saturation, and other circulatory parameters.

In some implementations, the PPG system 235 may be configured as a reflective PPG system 235 where the optical receiver(s) receive transmitted light that is reflected through the region of the user's finger. In some implementations, the PPG system 235 may be configured as a transmissive PPG system 235 where the optical transmitter(s) and optical receiver(s) are arranged opposite to one another, such that light is transmitted directly through a portion of the user's finger to the optical receiver(s).

The number and ratio of transmitters and receivers included in the PPG system 235 may vary. Example optical transmitters may include light-emitting diodes (LEDs). The optical transmitters may transmit light in the infrared spectrum and/or other spectrums. Example optical receivers may include, but are not limited to, photosensors, phototransistors, and photodiodes. The optical receivers may be configured to generate PPG signals in response to the wavelengths received from the optical transmitters. The location of the transmitters and receivers may vary. Additionally, a single device may include reflective and/or transmissive PPG systems 235.

The PPG system 235 illustrated in FIG. 2 may include a reflective PPG system 235 in some implementations. In these implementations, the PPG system 235 may include a centrally located optical receiver (e.g., at the bottom of the ring 104) and two optical transmitters located on each side of the optical receiver. In this implementation, the PPG system 235 (e.g., optical receiver) may generate the PPG signal based on light received from one or both of the optical transmitters. In other implementations, other placements, combinations, and/or configurations of one or more optical transmitters and/or optical receivers are contemplated.

The processing module 230-*a* may control one or both of the optical transmitters to transmit light while sampling the PPG signal generated by the optical receiver. In some implementations, the processing module 230-*a* may cause the optical transmitter with the stronger received signal to transmit light while sampling the PPG signal generated by the optical receiver. For example, the selected optical transmitter may continuously emit light while the PPG signal is sampled at a sampling rate (e.g., 250 Hz).

Sampling the PPG signal generated by the PPG system 235 may result in a pulse waveform that may be referred to as a "PPG." The pulse waveform may indicate blood pressure vs time for multiple cardiac cycles. The pulse waveform may include peaks that indicate cardiac cycles. Additionally, the pulse waveform may include respiratory induced variations that may be used to determine respiration rate. The processing module 230-*a* may store the pulse waveform in memory 215 in some implementations. The processing module 230-*a* may process the pulse waveform as it is generated and/or from memory 215 to determine user physiological parameters described herein.

The processing module 230-*a* may determine the user's heart rate based on the pulse waveform. For example, the processing module 230-*a* may determine heart rate (e.g., in beats per minute) based on the time between peaks in the pulse waveform. The time between peaks may be referred to as an interbeat interval (IBI). The processing module 230-*a* may store the determined heart rate values and IBI values in memory 215.

The processing module 230-*a* may determine HRV over time. For example, the processing module 230-*a* may determine HRV based on the variation in the IBIs. The processing module 230-*a* may store the HRV values over time in the memory 215. Moreover, the processing module 230-*a* may determine the user's respiratory rate over time. For example, the processing module 230-*a* may determine respiratory rate based on frequency modulation, amplitude modulation, or baseline modulation of the user's IBI values over a period of time. Respiratory rate may be calculated in breaths per minute or as another breathing rate (e.g., breaths per 30 seconds). The processing module 230-*a* may store user respiratory rate values over time in the memory 215.

The ring 104 may include one or more motion sensors 245, such as one or more accelerometers (e.g., 6-D accelerometers) and/or one or more gyroscopes (gyros). The motion sensors 245 may generate motion signals that indicate motion of the sensors. For example, the ring 104 may include one or more accelerometers that generate acceleration signals that indicate acceleration of the accelerometers. As another example, the ring 104 may include one or more gyro sensors that generate gyro signals that indicate angular motion (e.g., angular velocity) and/or changes in orientation. The motion sensors 245 may be included in one or more sensor packages. An example accelerometer/gyro sensor is a Bosch BM1160 inertial micro electro-mechanical system (MEMS) sensor that may measure angular rates and accelerations in three perpendicular axes.

The processing module 230-*a* may sample the motion signals at a sampling rate (e.g., 50 Hz) and determine the motion of the ring 104 based on the sampled motion signals. For example, the processing module 230-*a* may sample acceleration signals to determine acceleration of the ring 104. As another example, the processing module 230-*a* may sample a gyro signal to determine angular motion. In some implementations, the processing module 230-*a* may store motion data in memory 215. Motion data may include sampled motion data as well as motion data that is calculated based on the sampled motion signals (e.g., acceleration and angular values).

The ring 104 may store a variety of data described herein. For example, the ring 104 may store temperature data, such as raw sampled temperature data and calculated temperature data (e.g., average temperatures). As another example, the ring 104 may store PPG signal data, such as pulse waveforms and data calculated based on the pulse waveforms (e.g., heart rate values, IBI values, HRV values, and respiratory rate values). The ring 104 may also store motion data, such as sampled motion data that indicates linear and angular motion.

The ring 104, or other computing device, may calculate and store additional values based on the sampled/calculated physiological data. For example, the processing module 230 may calculate and store various metrics, such as sleep metrics (e.g., a Sleep Score), activity metrics, and readiness metrics. In some implementations, additional values/metrics may be referred to as "derived values." The ring 104, or other computing/wearable device, may calculate a variety of values/metrics with respect to motion. Example derived values for motion data may include, but are not limited to, motion count values, regularity values, intensity values, metabolic equivalence of task values (METs), and orientation values. Motion counts, regularity values, intensity values, and METs may indicate an amount of user motion (e.g., velocity/acceleration) over time. Orientation values may indicate how the ring 104 is oriented on the user's finger and if the ring 104 is worn on the left hand or right hand.

In some implementations, motion counts and regularity values may be determined by counting a number of acceleration peaks within one or more periods of time (e.g., one or more 30 second to 1 minute periods). Intensity values may indicate a number of movements and the associated intensity (e.g., acceleration values) of the movements. The intensity values may be categorized as low, medium, and high, depending on associated threshold acceleration values. METs may be determined based on the intensity of movements during a period of time (e.g., 30 seconds), the regularity/irregularity of the movements, and the number of movements associated with the different intensities.

In some implementations, the processing module 230-*a* may compress the data stored in memory 215. For example, the processing module 230-*a* may delete sampled data after making calculations based on the sampled data. As another example, the processing module 230-*a* may average data over longer periods of time in order to reduce the number of stored values. In a specific example, if average temperatures for a user over one minute are stored in memory 215, the processing module 230-*a* may calculate average temperatures over a five minute time period for storage, and then subsequently erase the one minute average temperature data. The processing module 230-*a* may compress data based on a variety of factors, such as the total amount of used/available memory 215 and/or an elapsed time since the ring 104 last transmitted the data to the user device 106.

Although a user's physiological parameters may be measured by sensors included on a ring 104, other devices may measure a user's physiological parameters. For example, although a user's temperature may be measured by a temperature sensor 240 included in a ring 104, other devices may measure a user's temperature. In some examples, other wearable devices (e.g., wrist devices) may include sensors that measure user physiological parameters. Additionally, medical devices, such as external medical devices (e.g., wearable medical devices) and/or implantable medical devices, may measure a user's physiological parameters. One or more sensors on any type of computing device may be used to implement the techniques described herein.

The physiological measurements may be taken continuously throughout the day and/or night. In some implementations, the physiological measurements may be taken during portions of the day and/or portions of the night. In some implementations, the physiological measurements may be taken in response to determining that the user is in a specific state, such as an active state, resting state, and/or a sleeping state. For example, the ring 104 can make physiological measurements in a resting/sleep state in order to acquire cleaner physiological signals. In one example, the ring 104 or other device/system may detect when a user is resting and/or sleeping and acquire physiological parameters (e.g., temperature) for that detected state. The devices/systems may use the resting/sleep physiological data and/or other data when the user is in other states in order to implement the techniques of the present disclosure.

In some implementations, as described previously herein, the ring 104 may be configured to collect, store, and/or process data, and may transfer any of the data described herein to the user device 106 for storage and/or processing. In some aspects, the user device 106 includes a wearable application 250, an operating system (OS) 285, a web browser application (e.g., web browser 280), one or more additional applications, and a GUI 275. The user device 106 may further include other modules and components, including sensors, audio devices, haptic feedback devices, and the like. The wearable application 250 may include an example of an application (e.g., "app") that may be installed on the user device 106. The wearable application 250 may be configured to acquire data from the ring 104, store the acquired data, and process the acquired data as described herein. For example, the wearable application 250 may include a user interface (UI) module 255, an acquisition module 260, a processing module 230-*b*, a communication module 220-*b*, and a storage module (e.g., database 265) configured to store application data.

The various data processing operations described herein may be performed by the ring 104, the user device 106, the servers 110, or any combination thereof. For example, in some cases, data collected by the ring 104 may be pre-processed and transmitted to the user device 106. In this example, the user device 106 may perform some data processing operations on the received data, may transmit the data to the servers 110 for data processing, or both. For instance, in some cases, the user device 106 may perform processing operations that require relatively low processing power and/or operations that require a relatively low latency, whereas the user device 106 may transmit the data to the servers 110 for processing operations that require relatively high processing power and/or operations that may allow relatively higher latency.

In some aspects, the ring 104, user device 106, and server 110 of the system 200 may be configured to evaluate sleep patterns for a user. In particular, the respective components of the system 200 may be used to collect data from a user via the ring 104, and generate one or more scores (e.g., Sleep Score, Readiness Score) for the user based on the collected data. For example, as noted previously herein, the ring 104 of the system 200 may be worn by a user to collect data from the user, including temperature, heart rate, HRV, and the like. Data collected by the ring 104 may be used to determine when the user is asleep in order to evaluate the user's sleep for a given "sleep day." In some aspects, scores may be calculated for the user for each respective sleep day, such that a first sleep day is associated with a first set of scores, and a second sleep day is associated with a second set of scores. Scores may be calculated for each respective sleep day based on data collected by the ring 104 during the respective sleep day. Scores may include, but are not limited to, Sleep Scores, Readiness Scores, and the like.

In some cases, "sleep days" may align with the traditional calendar days, such that a given sleep day runs from midnight to midnight of the respective calendar day. In other cases, sleep days may be offset relative to calendar days. For example, sleep days may run from 6:00 pm (18:00) of a calendar day until 6:00 pm (18:00) of the subsequent calendar day. In this example, 6:00 pm may serve as a "cut-off time," where data collected from the user before 6:00 pm is counted for the current sleep day, and data collected from the user after 6:00 pm is counted for the subsequent sleep day. Due to the fact that most individuals sleep the most at night, offsetting sleep days relative to calendar days may enable the system 200 to evaluate sleep patterns for users in such a manner that is consistent with their sleep schedules. In some cases, users may be able to selectively adjust (e.g., via the GUI) a timing of sleep days relative to calendar days so that the sleep days are aligned with the duration of time that the respective users typically sleep.

In some implementations, each overall score for a user for each respective day (e.g., Sleep Score, Readiness Score) may be determined/calculated based on one or more "contributors," "factors," or "contributing factors." For example, a user's overall Sleep Score may be calculated based on a set of contributors, including: total sleep, efficiency, restfulness, REM sleep, deep sleep, latency, timing, or any combination thereof. The Sleep Score may include any quantity of contributors. The "total sleep" contributor may refer to the sum of all sleep periods of the sleep day. The "efficiency" contributor may reflect the percentage of time spent asleep compared to time spent awake while in bed, and may be calculated using the efficiency average of long sleep periods (e.g., primary sleep period) of the sleep day, weighted by a duration of each sleep period. The "restfulness" contributor may indicate how restful the user's sleep is, and may be calculated using the average of all sleep periods of the sleep day, weighted by a duration of each period. The restfulness contributor may be based on a "wake up count" (e.g., sum of all the wake-ups (when user wakes up) detected during different sleep periods), excessive movement, and a "got up count" (e.g., sum of all the got-ups (when user gets out of bed) detected during the different sleep periods).

The "REM sleep" contributor may refer to a sum total of REM sleep durations across all sleep periods of the sleep day including REM sleep. Similarly, the "deep sleep" contributor may refer to a sum total of deep sleep durations across all sleep periods of the sleep day including deep sleep. The "latency" contributor may signify how long (e.g., average, median, longest) the user takes to go to sleep, and may be calculated using the average of long sleep periods throughout the sleep day, weighted by a duration of each period and the number of such periods (e.g., consolidation of a given sleep stage or sleep stages may be its own contributor or weight other contributors). Lastly, the "timing" contributor may refer to a relative timing of sleep periods within the sleep day and/or calendar day, and may be calculated using the average of all sleep periods of the sleep day, weighted by a duration of each period.

By way of another example, a user's overall Readiness Score may be calculated based on a set of contributors, including: sleep, sleep balance, heart rate, HRV balance, recovery index, temperature, activity, activity balance, or any combination thereof. The Readiness Score may include any quantity of contributors. The "sleep" contributor may refer to the combined Sleep Score of all sleep periods within the sleep day. The "sleep balance" contributor may refer to a cumulative duration of all sleep periods within the sleep day. In particular, sleep balance may indicate to a user whether the sleep that the user has been getting over some duration of time (e.g., the past two weeks) is in balance with the user's needs. Typically, adults need 7-9 hours of sleep a night to stay healthy, alert, and to perform at their best both mentally and physically. However, it is normal to have an occasional night of bad sleep, so the sleep balance contributor takes into account long-term sleep patterns to determine whether each user's sleep needs are being met. The "resting heart rate" contributor may indicate a lowest heart rate from the longest sleep period of the sleep day (e.g., primary sleep period) and/or the lowest heart rate from naps occurring after the primary sleep period.

Continuing with reference to the "contributors" (e.g., factors, contributing factors) of the Readiness Score, the "HRV balance" contributor may indicate a highest HRV average from the primary sleep period and the naps happening after the primary sleep period. The HRV balance contributor may help users keep track of their recovery status by comparing their HRV trend over a first time period (e.g., two weeks) to an average HRV over some second, longer time period (e.g., three months). The "recovery index" contributor may be calculated based on the longest sleep period. Recovery index measures how long it takes for a user's resting heart rate to stabilize during the night. A sign of a very good recovery is that the user's resting heart rate stabilizes during the first half of the night, at least six hours before the user wakes up, leaving the body time to recover for the next day. The "body temperature" contributor may be calculated based on the longest sleep period (e.g., primary sleep period) or based on a nap happening after the longest sleep period if the user's highest temperature during the nap is at least 0.5° C. higher than the highest temperature during the longest period. In some aspects, the ring may measure a user's body temperature while the user is asleep, and the system 200 may display the user's average temperature relative to the user's baseline temperature. If a user's body temperature is outside of their normal range (e.g., clearly above or below 0.0), the body temperature contributor may be highlighted (e.g., go to a "Pay attention" state) or otherwise generate an alert for the user.

In some aspects, the system 200 may include rings 104 manufactured with an outer cover, or outer housing 205-*b*, that is capable of rotating around an inner cover, or inner housing 205-*a*, of the ring 104. For example, a set of side covers may be coupled to the inner housing 205-*a* in a fixed manner (e.g., statically coupled), while the inner housing 205-*b* may be coupled to the set of side covers in a non-fixed, or slidable, manner (e.g., non-statically coupled). In such cases, the inner housing 205-*b* may be able to "slide" along the side covers to allow the inner housing 205-*b* to freely rotate relative to the inner housing 205-*a*, including one or more sensors, such as the PPG system 235, temperature sensors 204, motion sensors 245, or any combination thereof. As such, the outer housing 205-*b* may rotate around the inner housing 205-*a*, and the one or more sensors, under an applied force, such that the inner housing 205-*a* remains in a fixed position relative to a finger of a user 102, and measurement points used by the one or more sensors do not change (e.g., remain the same) as the outer housing 205-*b* rotates. In some examples, the outer housing 205-*b* may rotate freely (e.g., un-restricted) around the inner housing 205-*a* while, in some other examples, the outer housing 205-*b* may rotate in a defined (e.g., restricted) range of motion, where the range of motion is limited based on one or more stopping components in the wearable ring device.

In some cases, other mechanical components, such as bearings (e.g., or bushings) may be used to enable the outer housing 205-*b* to rotate relative to the inner housing 205-*a*. As such, in cases where the ring 104 is inadvertently bumped into an object (e.g., exposed to an external force), the outer housing 205-*b* may be configured to rotate in response to the external force, thereby preventing the entire ring 104 from rotating, and enabling the measurement points to remain stationary (e.g., sensors stay facing the palm-side of the finger of the user 102).

Figure 3:
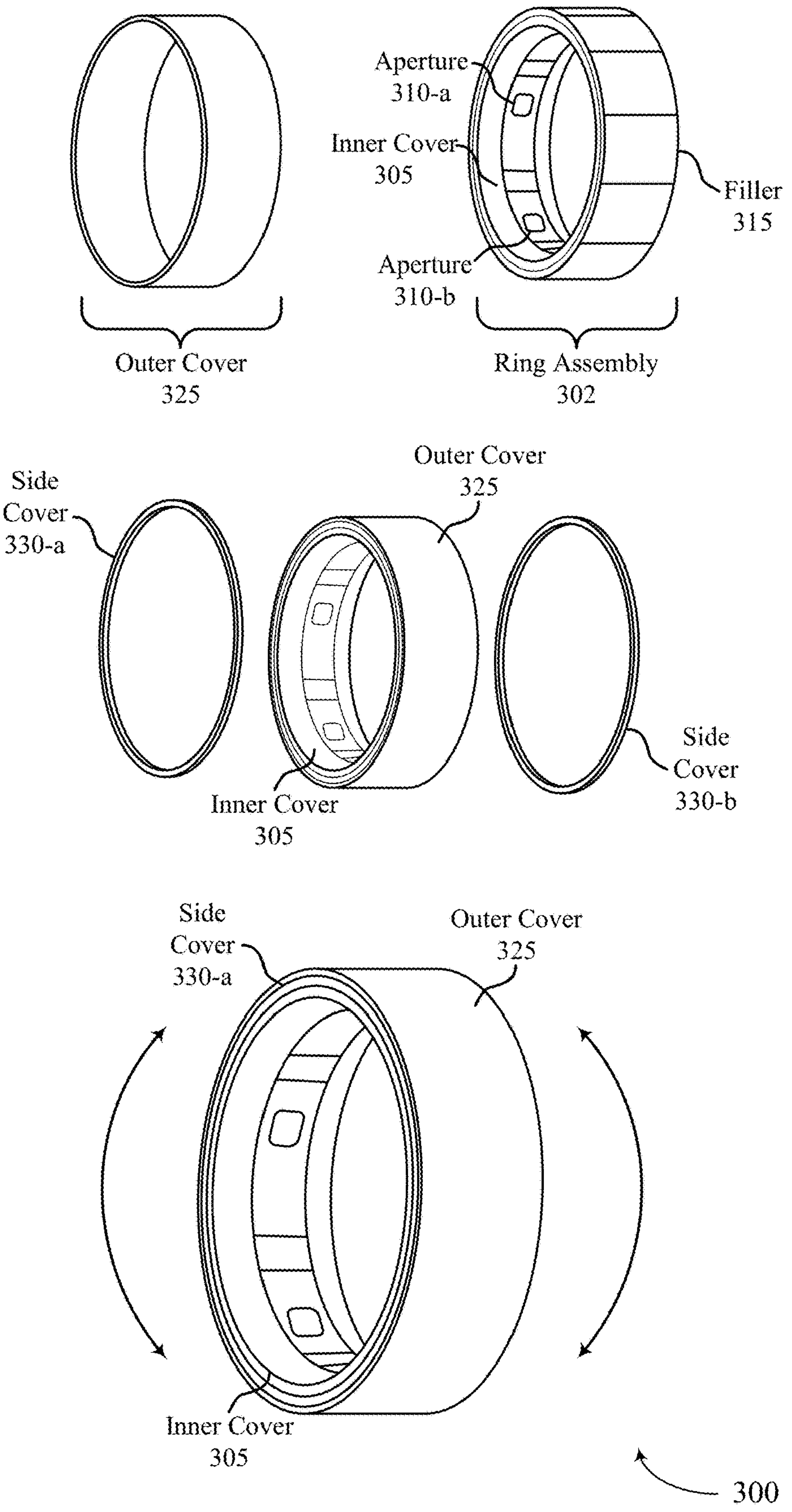
FIG. 3 shows an example of a system that supports techniques for manufacturing a wearable ring device with an outer cover capable of rotation in accordance with aspects of the present disclosure.

FIG. 3 shows an example of a system 300 that supports techniques for manufacturing a wearable ring device with an outer cover capable of rotation in accordance with aspects of the present disclosure. In other words, the system 300 may support techniques for a ring 104 to be manufactured "inside out," securing an outer cover 325 to an inner cover 305, including electrical components of the ring 104, in a non-static manner that enables the outer cover 325 to rotate when exposed to an external force.

For example, each sensor (e.g., of one or more sensors) of the ring 104 may collect physiological data with reference to one or more measurement points on a finger of a user 102. The term "measurement point" may refer to a radial position or location on the finger of the user 102 (e.g., relative to the ring 104) where a sensor performs physiological measurements. In such cases, the measurement point may be one or more of an optical measurement point, an electrical measurement point, a tactile measurement point, or the like thereof. Due to physiology of the human finger, the ring 104 may achieve the best signal and highest data quality when the one or more sensors are facing the palm-side of the finger. In other words, the one or more sensors may achieve the best signal and highest data quality when the one or more sensors collect physiological data with reference to a measurement point on a palm side of the finger of the user 102.

However, in some cases, the ring 104 may be inadvertently rotated around the finger of the user 102 due to an external force, such as the user 102 bumping their hand on a surface, resulting in a change of position of the one or more sensors relative to the finger of the user 102. As such, the one or more measurement points associated with each sensor of the ring 104 may change (e.g., each sensor may become rotated to measurement points on dorsal side of the finger of the user 102), such that the physiological data collected by the ring 104 is associated with one or more new measurement points (e.g., at new radial positions or locations on the finger of the user 102). However, the user 102, the ring 104, or both, may be unaware that the ring 104 was rotated and, as such, may interpret associated changes in collected physiological data as being based on a change in the user 102, rather than due to a change of measurement point, reducing accuracy of the collected physiological data.

Accordingly, techniques described herein may support manufacturing of a ring 104 (e.g., in the system 300) to enable an outer cover of the ring 104 to rotate relative to the rest of the ring 104. Specifically, the electrical components of the ring 104 (e.g., the PCB and one or more optical sensors) may be attached to an inner cover 305 (e.g., inner ring-shaped housing) of the ring 104 to form a ring assembly 302 (e.g., ring engine assembly). In some cases (e.g., as depicted in FIG. 3), to form the ring assembly 302, the inner cover 305 (e.g., and attached electrical components) may be placed into a mold, such that a filler 315, such as a clear epoxy, may be injected into the mold to secure the electrical components to the inner cover 305. Additionally, the injection molding may cause the filler 315 to fill one or more apertures 310 of the inner cover 305, such as an aperture 310-*a* and an aperture 310-*b*, such that the one or more optical sensors may be secured with relation to the apertures 310 to enable data collection. The result of injection molding the inner cover 305 to the electrical components may be referred to as the ring assembly 302 (e.g., ring engine assembly). Alternatively, electrical components may be attached to the inner cover 305 without the use of the filler 315. In other words, the ring assembly 302 may be manufactured without the use of injection molding (e.g., without the filler 315).

The ring assembly 302 may essentially be an operational ring 104 without an outer cover 325 (e.g., outer ring-shaped housing). Subsequently, an outer cover 325 may be slid around the inner cover 305 (e.g., ring assembly 302) and may be secured to the inner cover 305 in a non-static manner to finish the ring. In some cases, the outer cover 325 may be secured to the inner cover 305 using one or more side covers 330 (e.g., ring-shaped fittings), such as the side cover 330-*a* and the side cover 330-*b*. For example, the side cover 330-*a* and the side cover 330-*b* may be coupled to the inner cover 305 (e.g., and/or ring assembly) in a fixed manner (e.g., statically coupled), while the side cover 330-*a* and the side cover 330-*b* may be coupled to the outer cover 325 in a non-fixed, or slidable, manner (e.g., non-statically coupled). In such cases, the outer cover 325 may be able to "slide" along the side covers 330 to allow the outer cover 325 to rotate relative to the inner cover 305 (e.g., relative to the ring assembly 302), including the one or more sensors. As such, the outer cover 325 may rotate around the inner cover 305 (e.g., and the one or more sensors) under an applied force (e.g., an external force), such that the inner cover remains in a fixed position relative to the finger of the user 102 (e.g., remains stationary on the finger). Further, the measurement points used by the one or more sensors may not change (e.g., remain the same) as the outer cover 325 rotates due to the inner cover 305 remaining in the fixed position.

Additionally, or alternatively, other mechanical components, such as bearings (e.g., or bushings) may be used to enable the outer cover 325 to rotate relative to the inner cover 305. In other words, the inner cover 305 (e.g., the ring assembly 302), the outer cover 325, the side covers 330, or any combination thereof, may include one or more other mechanical components that, when coupled together, may enable rotation of the outer cover 325 relative to the inner cover 305. As such, as described previously, in cases where the ring 104 is inadvertently bumped into an object (e.g., exposed to an external force), the outer cover 325 may be configured to rotate in response to the external force, thereby preventing the entire ring 104 from rotating, and enabling the measurement points to remain stationary (e.g., sensors stay facing the palm-side of the finger of the user 102).

In some examples, the ring 104 may include one or more other components, which may be referred to as stopping components, to limit a range of rotation of the outer cover 325. In other words, without the one or more stopping components, the outer cover 325 may freely rotate, or be capable of completing a full rotation (e.g., 360 degrees of rotation), around the inner cover 305. In other words, the range of rotation may be 360 degrees around an origin of the ring 104. As such, the outer cover 325, the inner cover 305 (e.g., or the ring assembly 302), the side covers 330, or any combination thereof, may include one or more stopping components to limit rotation of the outer cover 325 to a predefined range. For example, the one or more stopping components may be positioned with the ring 104 such that the outer cover 325 may be capable of completing a half rotation (e.g., 180 degrees of rotation), around the inner cover 305. In other words, the range of rotation may be 180 degrees around an origin of the ring 104.

Additionally, or alternatively, the one or more stopping components may disable rotation of the outer cover 325 around the inner cover 305 (e.g., limit rotation of the outer cover 325 to a range of zero degrees). For example, the one or more stopping components may be enabled, or activated, by a user 102, such that the one or more stopping components may prevent the outer cover 325 from rotating around the inner cover 305 when enabled. For example, the user 102 may activate the one or more stopping components based on applying pressure to the ring 104 (e.g., outer cover 325) for a threshold duration or based on inputting a sequence of rotations associated with activating the one or more stopping components (e.g., associated with stopping rotation of the outer cover 325). Similarly, the one or more stopping components may be disabled, or deactivated, by the user 102, such that the outer cover 325 may rotate around the inner cover 305 (e.g., freely or within the predefined range). The user 102 may deactivate the one or more stopping components in a similar manner to activation of the one or more stopping components.

Additionally, or alternatively, the ring 104 may include one or more other components, which may be referred to as spring components, that enables the outer cover 325 of the ring 104 to return to an initial, or reference, position after rotation (e.g., if the outer cover 325 is rotated within a threshold range of rotation). For example, the initial position may be defined as a position of the outer cover 325 relative to the inner cover 305 when the one or more sensors of the ring 104 are facing the palm-side of the finger of the user 102. As such, the outer cover 325 may rotate clockwise, counterclockwise, or both, within a range of rotation defined for the outer cover 325 (e.g., based on the one or more stopping components) and may return to the initial position following rotation based on the one or more spring components. In some examples, the range of rotation may be defined relative to the initial position. For example, an entire range of rotation for the outer cover 305 may be 180 degrees of rotation (e.g., relative to the origin of the ring 104), however, the entire range of rotation may include 90 degrees of rotation (e.g., relative to the origin of the ring 104) clockwise from the initial position and 90 degrees of rotation counterclockwise from the initial position.

Though described in the context of side covers 330, other mechanical components, or both, this is not to be regarded as a limitation of the present disclosure. In this regard, other techniques may be employed to enable the outer cover 325 to rotate around the inner cover 305 (e.g., the ring assembly 302). For example, in some cases, the outer cover 325 may include one or more grooves that are configured to be slidably coupled to one or more protrusions that extend from the inner cover 305.

Figure 4:
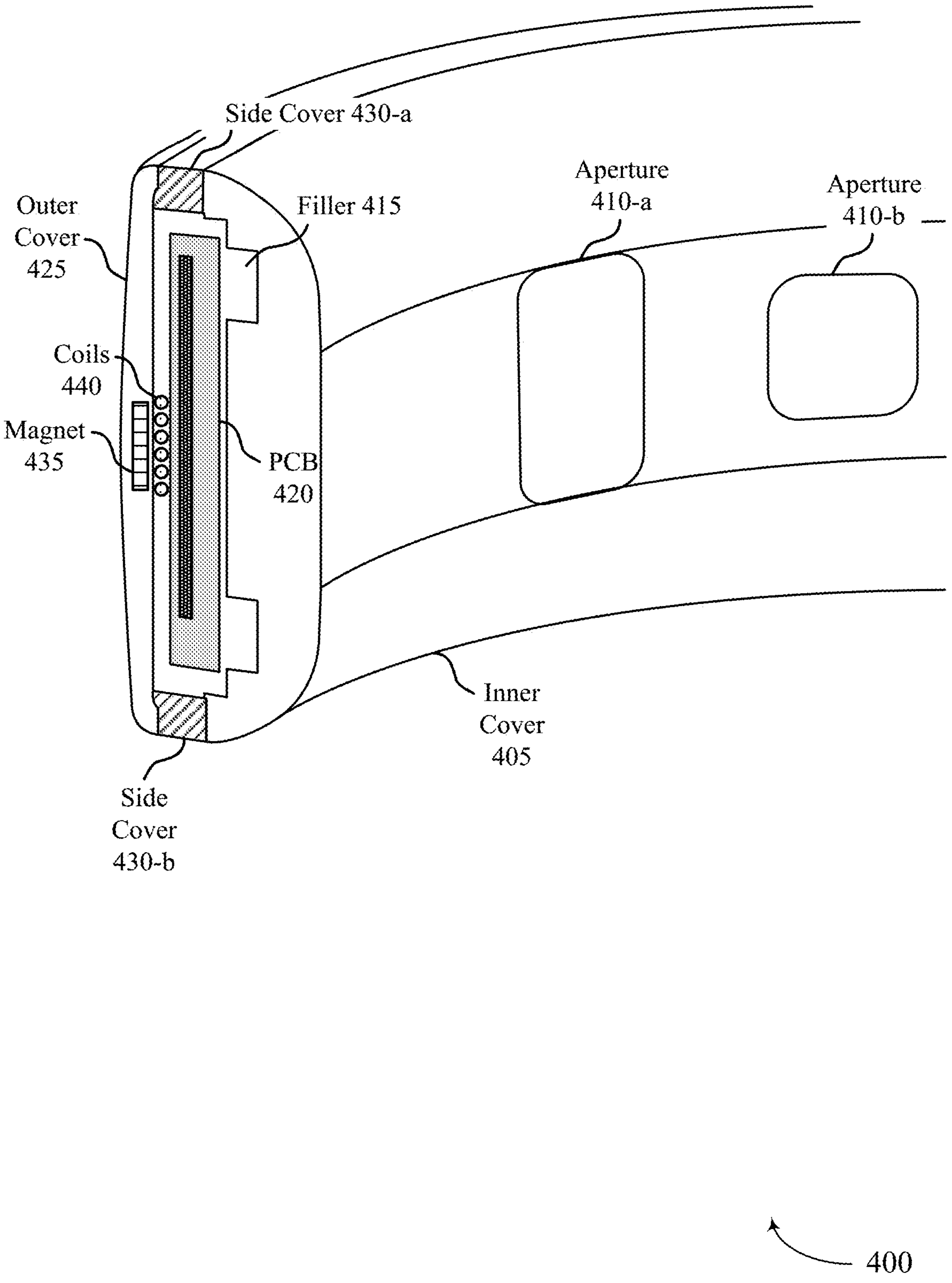
FIG. 4 shows an example of a cross-sectional view of a wearable ring that supports techniques for manufacturing a wearable ring device with an outer cover capable of rotation in accordance with aspects of the present disclosure.

FIG. 4 shows an example of a cross-sectional view 400 that supports techniques for manufacturing a wearable ring device with an outer cover capable of rotation in accordance with aspects of the present disclosure.

In some examples, as described with reference to FIG. 3, side covers 430 (e.g., a side cover 430-*a* and a side cover 430-*b*) of a ring 104 may be coupled to an inner cover 405 of the ring 104 in a fixed manner, while the side covers 430 may be coupled to an outer cover 425 of the ring 104 in a non-fixed manner, such that the outer cover 425 may rotate relative to the inner cover 405. For example, as depicted in the cross-sectional view 400, a ring engine assembly (e.g., a ring assembly 302 as described with reference to FIG. 3) may be manufactured by attaching electrical components of the ring 104, such as a PCB 420 and one or more sensors (e.g., among other electrical components), to the inner cover 405 (e.g., inner ring-shaped housing) and placing the inner cover 405 and attached electrical components in a mold. As such, filler 415 may be injected into the mold, such that the electrical components of the ring 104 are secured to the inner cover 405. Additionally, injecting filler 415 into the mold may result in the filler 415 filling one or more apertures 410 of the inner cover 405 (e.g., of the ring 104), such as an aperture 410-*a* and an aperture 410-*b*, such that the one or more sensors, aligned with the apertures 410, may collect data (e.g., physiological data) via transmission of signaling (e.g., light) through the apertures 410. Alternatively, the ring engine assembly may be manufactured without the use of filler 415. In other words, the electrical components may be attached to the inner cover 405 in a semi-permanent manner, such that injection molding of the filler 415 is not needed to secure the electrical components to the inner cover 405.

Subsequently, as described with reference to FIG. 3, the outer cover 425 may be slid, or placed, around the inner cover 405 (e.g., ring engine assembly) and may be secured to the inner cover 405 in a non-static manner using side covers 430 (e.g., ring-shaped fittings), such as the side cover 430-*a* and the side cover 430-*b*, to finish the ring. For example, the side cover 430-*a* and the side cover 430-*b* may be coupled to the inner cover 405 (e.g., and/or ring assembly) in a fixed manner (e.g., statically coupled), while the side cover 430-*a* and the side cover 430-*b* may be coupled to the outer cover 425 in a non-fixed, or slidable, manner (e.g., non-statically coupled). In such cases, the outer cover 425 may be able to “slide” along the side covers 430 to allow the outer cover 425 to rotate relative to the inner cover 405 (e.g., relative to the ring assembly), including the one or more sensors. As such, the outer cover 425 may rotate around the inner cover 405 (e.g., and the one or more sensors) under an applied force (e.g., an external force), such that the inner cover remains in a fixed position relative to the finger of the user 102 (e.g., remains stationary on the finger), or otherwise reduce movement of the inner cover relative to the user’s finger. Further, the measurement points used by the one or more sensors may not change (e.g., remain the same) as the outer cover 425 rotates due to the inner cover 405 remaining in the fixed position.

In some cases, the rotation of the outer cover 425 relative to the inner cover 405 (e.g., ring engine assembly) may support energy-harvesting procedures. In other words, a user 102 may perform a wireless charging procedure for the ring 104 based on rotating the outer cover 425 relative to the inner cover 405. For example, one or more components of the ring 104, such as the ring engine assembly, the inner cover 405, the outer cover 425, or any combination thereof, may include one or more wireless charging elements, or components, such that rotation of the outer cover 425 relative to the inner cover 405 generates an energy signal (e.g., current, charge) via the wireless charging elements, where the energy signal is used to charge a battery of the ring 104 (e.g., in the ring engine assembly).

As an illustrative example, as depicted in FIG. 4, the one or more wireless charging components may be inductive charging components, including one or more magnets 435 and one or more coils 440 (e.g., inductive coils 440). The one or more magnets 435 may be positioned at least partially within the outer cover 425 and the one or more coils 440 may be positioned at least partially within the ring engine assembly (e.g., including the inner cover 405). Additionally, the one or more magnets 435 may be positioned relative to the one or more coils 440 such that rotation of the outer cover 425 relative to the inner cover 405 (e.g., ring engine assembly), or rotation of the one or more magnets 435 relative to the one or more coils 440, causes the one or more magnets 435 of the outer cover 425 to induce an electrical current within the one or more coils 440 of the inner cover 405, where the electrical current is used to charge the battery of the wearable ring device, power components of the wearable ring device, or both. In some examples, a threshold quantity of rotations of the outer cover 425 relative to the inner cover 405 may initiate the wireless charging procedure. For example, the ring 104 may refrain from initiating the wireless charging procedure due to accidental rotation of the outer cover 425 relative to the inner cover 405.

In some examples, the wearable ring device may include one or more LEDS that emit light while the ring 104 performs the wireless charging procedure. For example, the one or more LEDs may be positioned at least partially within the outer cover 425, the inner cover 405, the ring engine assembly, the side covers 430, or any combination thereof, such that the one or more LEDs emit light while the outer cover 425 rotates around the inner cover 405 during the wireless charging procedure. In some examples, the one or more LEDs may begin emitting light based on the battery receiving a charge (e.g., a threshold charge) as a result of the wireless charging procedure (e.g., may not emit a light prior to charging beginning). Additionally, or alternatively, the one or more LEDs may begin emitting light based on a threshold quantity of rotations of the outer cover 425 relative to the inner cover 405 being completed (e.g., may not emit light due to accidental or incomplete rotation(s)).

Though described in the context of an inductive charging procedure, this is not to be regarded as a limitation of the present disclosure. In this regard, any wireless charging procedure or mechanisms that uses motion (e.g., rotation) to charge a battery may be employed with reference to the techniques described herein.

Figure 5:
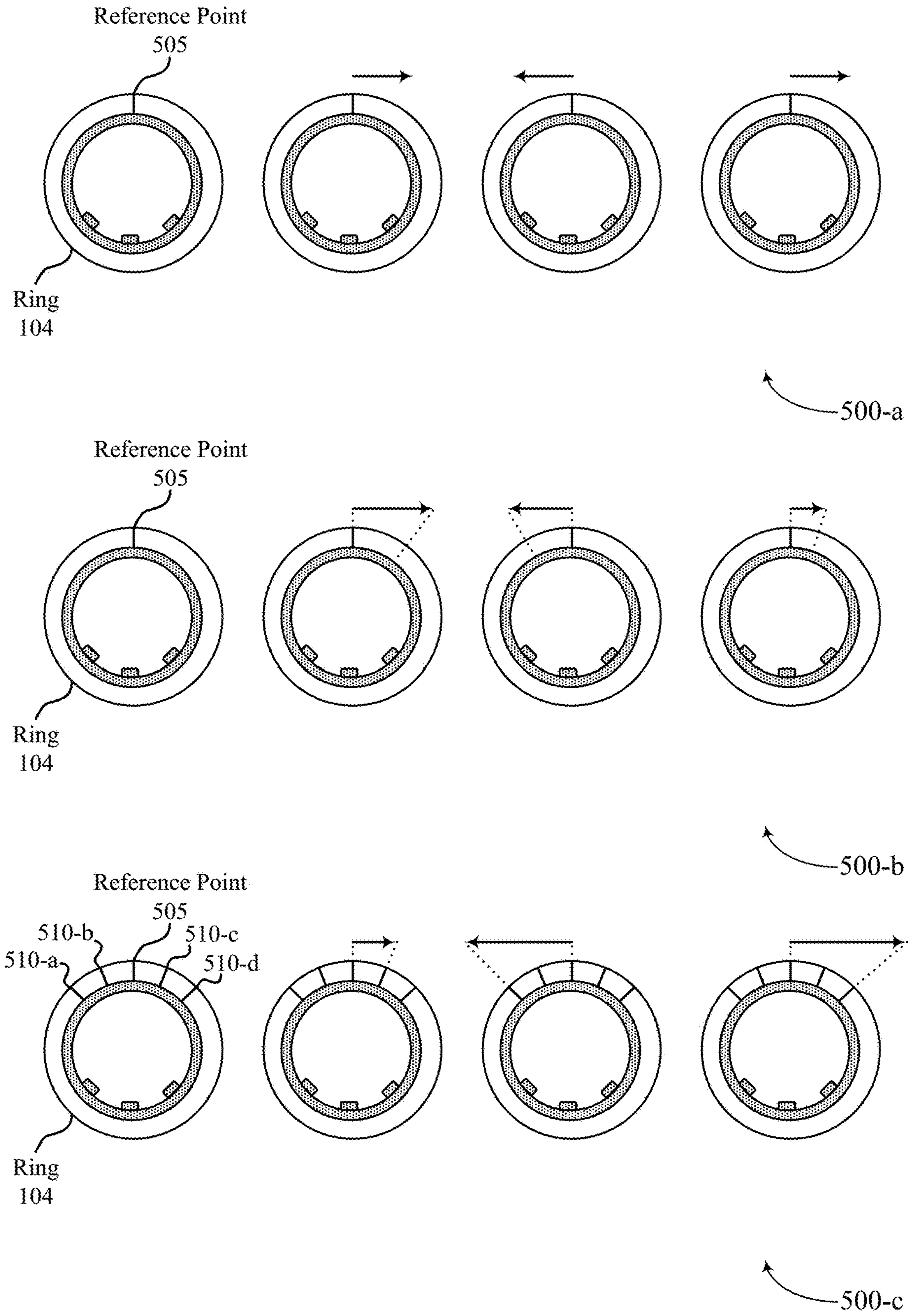
FIG. 5 shows an example of command patterns that supports techniques for manufacturing a wearable ring device with an outer cover capable of rotation in accordance with aspects of the present disclosure.

FIG. 5 shows examples of command patterns 500 (e.g., a command pattern 500-*a*, a command pattern 500-*b*, and a command pattern 500-*c*) that supports techniques for manufacturing a wearable ring device with an outer cover capable of rotation in accordance with aspects of the present disclosure.

In some examples, as described with reference to FIG. 3, side covers of a ring 104 may be coupled to an inner cover (e.g., ring engine assembly) of the ring 104 in a fixed manner, while the side covers may be coupled to an outer cover of the ring 104 in a non-fixed manner, such that the outer cover 425 may rotate relative to the inner cover 405. In such cases, rotation of the outer cover relative to the inner cover may enable a user 102 to input one or more ring-inputted commands via the rotation. For example, the ring 104 may be associated with a reference point 505 (e.g., an initial position), where the reference point 505 indicates an initial, or starting position, of the outer cover relative to the inner cover. In some examples, as described with reference to FIG. 3, the ring 104 may include one or more spring (and/or magnetic) components to return the outer cover to the reference point 505 following rotation of the outer cover.

As such, one or more sensors of the ring 104 may identify when the outer cover is rotated (e.g., freely or within a defined range of rotation, described with reference to FIG. 3) relative to the reference point 505 and may identify one or more rotations of the outer cover, where the one or more rotations define a sequence of rotations. Additionally, respective components of a system associated with the ring 104 (e.g., including the ring 104, among other components) may compare the input, or identified, sequence of rotations with a set of configured sequences of rotations (e.g., reference sequences) associated with (e.g., defined for) the ring 104. Each configured sequence of rotation (e.g., each reference sequence) of the set of configured sequences of rotations may be associated with a ring-inputted command, such that when an input sequence of rotation matches a configured sequence of rotations (e.g., as identifier by the ring 104 or the system associated with the ring 104), the system may generate a signal to execute, or perform, the ring-inputted command associated with the configured sequence of rotations. As such, a user 102 may define configured sequences of rotations and correlate, or pair, them to ring-inputted commands, such that the user 102 may input a command via the ring 104 rather than via a user device 106 associated with the ring 104.

In some examples, as described with reference to the command pattern 500-*a*, the one or more sensors may identify a direction of rotation (e.g., clockwise or counterclockwise) of each rotation in a sequence of rotations, such that the input sequence of rotations is based on the direction of each rotation in the input sequence of rotations. For example, the one or more sensors may identify that the outer cover is rotated clockwise relative to the reference point 505, counterclockwise relative to the reference point 505, and then clockwise relative to the reference point 505. Thus, the system may identify that the user 102 input a sequence of rotations defined by the clockwise rotation followed by the counterclockwise rotation followed by the clockwise rotation. As such, the system may compare the input sequence of rotations to the set of configured sequences of rotations and may identify that a first configured sequence of rotations of the set of configured sequences of rotations is also defined by the clockwise rotation followed by the counterclockwise rotation followed by the clockwise rotation. Thus, the system may match the input sequence of rotations with the first configured sequence of rotations and perform a ring-inputted command associated with the first configured sequence of rotations. For example, the ring-inputted command associated with the first configured sequence of rotations may cause the system to skip a song playing via a music application on a user device 106 associated with the ring 104 (e.g., associated with the system).

Additionally, the one or more sensors may identify a magnitude of rotation, which may simply be referred to as magnitude, of each rotation in a sequence of rotations, such that the input sequence of rotations is based on a direction of each rotation in the input sequence of rotations, a magnitude of each rotation in the input sequence of rotations, or both. For example, the one or more sensors may be configured to identify an end position of the outer cover associated with a rotation and may compare the end position with the reference point 505 (e.g., initial position) to determine an angular (e.g., or radial) difference between the end position and the reference point 505, where the angular difference defines the magnitude of the rotation. In some examples, rotations of each configured sequence of rotations may be associated with a magnitude tolerance. In other words, the system may identify that a rotation of an input sequence of rotations matches a rotation of a configured sequence of rotations based on a magnitude of the input rotation being within the magnitude tolerance (e.g., threshold magnitude) of a magnitude of the configured rotation.

For example, as depicted in the command pattern 500-*b*, the system may identify that the outer cover is rotated clockwise relative to the reference point 505 at a first magnitude, counterclockwise relative to the reference point 505 at a second magnitude, then clockwise relative to the reference point 505 at a third magnitude. Thus, the system may identify that the user 102 input a sequence of rotations defined by the clockwise rotation associated with the first magnitude followed by the counterclockwise rotation associated with the second magnitude followed by the clockwise rotation associated with the third magnitude. As such, the system may compare the input sequence of rotations to the set of configured sequences of rotations and may identify that a second configured sequence of rotations of the set of configured sequences of rotations is also defined by the clockwise rotation associated with the first magnitude followed by the counterclockwise rotation associated with the second magnitude followed by the clockwise rotation associated with the third magnitude. Thus, the system may match the input sequence of rotations with the second configured sequence of rotations and perform a ring-inputted command associated with the second configured sequence of rotations. For example, the ring-inputted command associated with the second configured sequence of rotations may cause the system to initiate an activity session.

Additionally, or alternatively, the ring 104 may include one or more indexing components and the one or more sensors may identify an index 510 associated with each rotation in a sequence of rotations, such that the input sequence of rotations is based on an index 510 associated with each rotation in the input sequence of rotations. For example, as described with reference to the command pattern 500-*c*, the one or more indexing components may define an index 510-*a*, an index 510-*b*, an index 510-*c*, and an index 510-*d*. In some cases, the indexes 510 may be defined visually (e.g., visual indexing components). In other words, each index 510 may be associated with a line or a marker on the ring 104, such that the user 102 may identify each index 510 based on lines. Additionally, or alternatively, the indexes 510 may be defined auditorily (e.g., auditory indexing components). In other words, each index 510 may be associated with one or more beeps, or chimes, such that the user 102 may identify each index 510 based on the one or more beeps, or chimes. Additionally, or alternatively, the indexes 510 may be defined tactilely (e.g., tactile indexing components). In other words, each index 510 may be associated with one or more vibrations or ridges, such that the user 102 may identify each index 510 based on the one or more vibrations or ridges.

In some examples, the one or more sensors may identify that a rotation is associated with a specific index 510 based on a magnitude of the input rotation being with a threshold magnitude (e.g., magnitude tolerance) of a magnitude associated with the specific index 510. For example, the index 510-*a* may be associated with a 30 degree, counterclockwise rotation of the outer cover relative to an origin of the ring 104 and relative to the reference point 505. Additionally, the threshold magnitude may be 3 degrees, such that a counterclockwise rotation between 33 degrees and 27 degrees may be associated with the index 510-*a*.

For example, as described with reference to the command pattern 500-*c*, the system may identify that the outer cover is rotated to the index 510-*c*, to the index 510-*a*, and then to the index 510-*d*. Thus, the system may identify that the user 102 input a sequence of rotations defined by the rotation associated with the index 510-*c* followed by the rotation associated with index 510-*a*, followed by the rotation associated with the index 510-*d*. As such, the system may compare the input sequence of rotations to the set of configured sequences of rotations and may identify that a third configured sequence of rotations of the set of configured sequences of rotations is also defined by the rotation associated with the index 510-*c* followed by the rotation associated with index 510-*a*, followed by the rotation associated with the index 510-*d*. Thus, the system may match the input sequence of rotations with the third configured sequence of rotations and perform a ring-inputted command associated with the third configured sequence of rotations. For example, the ring-inputted command associated with the third configured sequence of rotations may cause the system to put a user device 106 associated with the ring 104 in a "Do Not Disturb" mode that silences notifications.

In some examples, the system may define a threshold duration between each rotation in a sequence of rotations for the input sequence of rotations to be considered valid. For example, the system may identify that a duration between a first rotation of a sequence of rotations and a second rotation of the sequence of rotations failed to satisfy (e.g., exceeded) the threshold duration. Thus, the system may assume that the first rotation, the second rotation, or both, were unintentional (e.g., not intentionally input by the user) and may refrain from identifying the sequence of rotations, refrain from comparing the sequence of rotations to the set of configured sequences of rotations, or both (e.g., may determine the input sequence of rotations was not valid). In such cases, the system may determine that an input sequence of rotations is not valid based on a threshold quantity of durations (e.g., at least one duration) between rotations of the input sequence of rotation failing to satisfy the threshold duration. Conversely, the system may identify that the duration between the first rotation of the sequence of rotations and the second rotation of the sequence of rotations satisfied (e.g., did not exceed) the threshold duration. As such, the system may proceed with identifying the sequence of rotations and comparing the sequence of rotations to the set of configured sequences of rotations (e.g., based on determining the input sequence of rotations was valid, or intentional).

Additionally, or alternatively, the system may define a threshold magnitude of each rotation in a sequence of rotations for the sequence of rotations to be considered valid. For example, the system may identify that a magnitude of a first rotation of a sequence of rotations failed to satisfy (e.g., did not exceed or exceeded) the threshold magnitude. Thus, the system may assume that the first rotation was unintentional (e.g., not intentionally input by the user) and may refrain from identifying the sequence of rotations, refrain from comparing the sequence of rotations to the set of configured sequences of rotations, or both (e.g., may determine the input sequence of rotations was not valid). In such cases, the system may determine that an input sequence of rotations is not valid based on a threshold quantity of rotations (e.g., at least one rotation) of the input sequence of rotation being associated with magnitudes that fail to satisfy the threshold magnitude. Conversely, the system may identify that the magnitude of the first rotation satisfied (e.g., exceeded or did not exceed) the threshold magnitude. As such, the system may proceed with identifying the sequence of rotations and comparing the sequence of rotations to the set of configured sequences of rotations (e.g., based on determining the input sequence of rotations was valid, or intentional).

Figure 6:
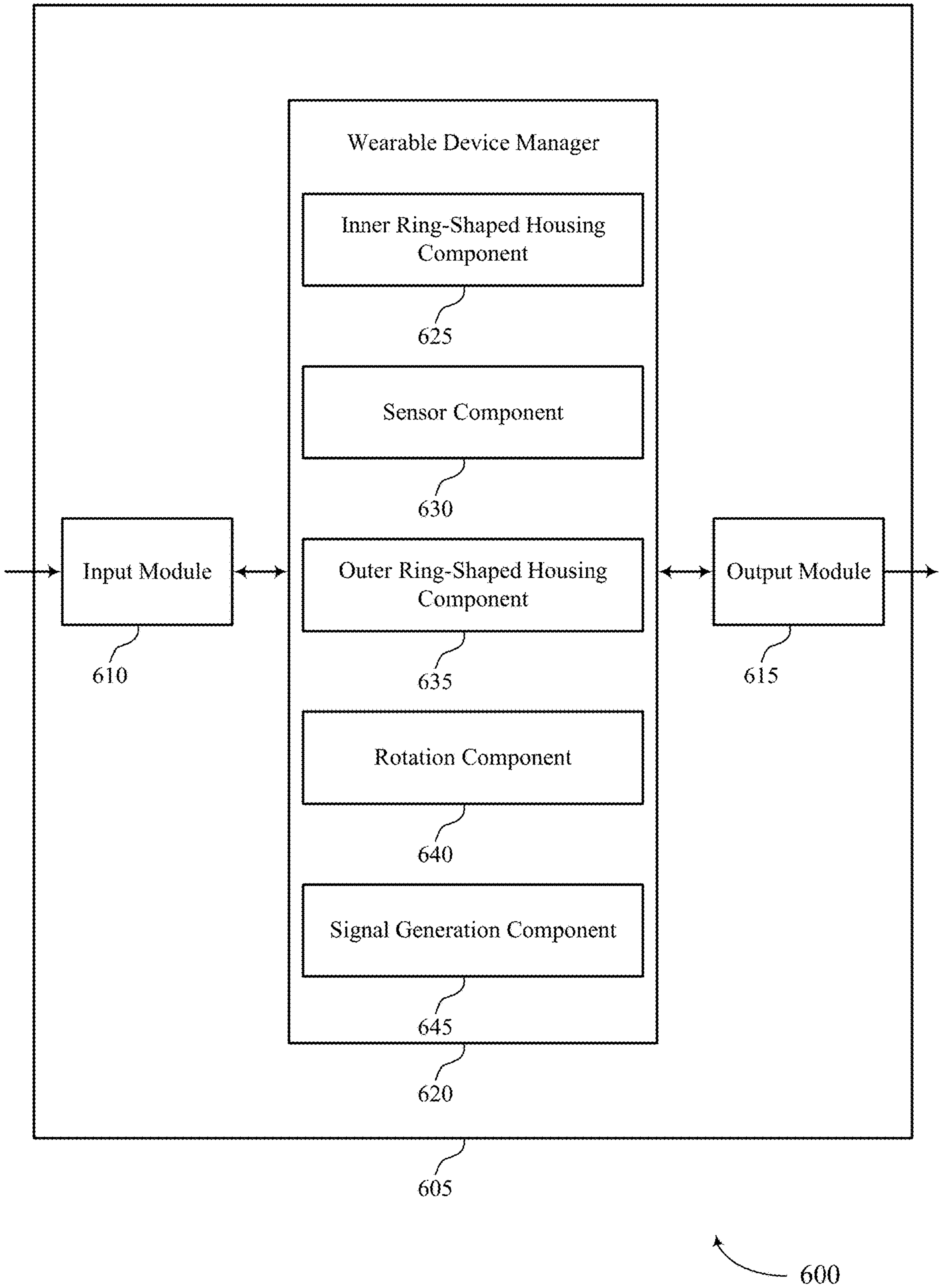
FIG. 6 shows a block diagram of an apparatus that supports techniques for manufacturing a wearable ring device with an outer cover capable of rotation in accordance with aspects of the present disclosure.

FIG. 6 shows a block diagram 600 of a device 605 that supports techniques for manufacturing a wearable ring device with an outer cover capable of rotation in accordance with aspects of the present disclosure. The device 605 may include an input module 610, an output module 615, and a wearable device manager 620. The device 605, or one or more components of the device 605 (e.g., the input module 610, the output module 615, and the wearable device manager 620), may include at least one processor, which may be coupled with at least one memory, to support the described techniques. Each of these components may be in communication with one another (e.g., via one or more buses).

For example, the wearable device manager 620 may include an inner ring-shaped housing component 625, a sensor component 630, an outer ring-shaped housing component 635, a rotation component 640, a signal generation component 645, or any combination thereof. In some examples, the wearable device manager 620, or various components thereof, may be configured to perform various operations (e.g., receiving, monitoring, transmitting) using or otherwise in cooperation with the input module 610, the output module 615, or both. For example, the wearable device manager 620 may receive information from the input module 610, send information to the output module 615, or be integrated in combination with the input module 610, the output module 615, or both to receive information, transmit information, or perform various other operations as described herein.

The inner ring-shaped housing component 625 may be configured as or otherwise support a means for an inner ring-shaped housing comprising one or more apertures, wherein the inner ring-shaped housing defines an inner circumferential surface of the wearable ring device. The sensor component 630 may be configured as or otherwise support a means for one or more sensors disposed at least partially within the inner ring-shaped housing, the one or more sensors configured to acquire physiological data from a user through the one or more apertures, wherein the one or more sensors acquire the physiological data at one or more measurement points at one or more radial positions on a circumference of a finger of the user. The outer ring-shaped housing component 635 may be configured as or otherwise support a means for an outer ring-shaped housing that at least partially surrounds the inner ring-shaped housing, wherein the outer ring-shaped housing defines an outer circumferential surface of the wearable ring device, wherein the outer ring-shaped housing is non-statically coupled with the inner ring-shaped housing such that the outer ring-shaped housing is configured to rotate relative to the inner ring-shaped housing, and wherein the inner ring-shaped housing is configured to remain stationary relative to the finger of the user during rotation of the outer ring-shaped housing such that the one or more measurement points remain unchanged during rotation of the outer ring-shaped housing.

Additionally, or alternatively, the wearable device manager 620 may support operating a wearable ring device in accordance with examples as disclosed herein. The sensor component 630 may be configured as or otherwise support a means for collecting physiological data associated with a user via one or more sensors of the wearable ring device, wherein the one or more sensors acquire the physiological data at one or more measurement points at one or more radial positions on a circumference of a finger of the user, wherein the wearable ring device comprises an inner ring-shaped housing and an outer ring-shaped housing. The rotation component 640 may be configured as or otherwise support a means for rotating the outer ring-shaped housing of the wearable ring device around the inner ring-shaped housing, wherein the inner ring-shaped housing of the wearable ring device remains stationary during rotation of the outer ring-shaped housing such that the one or more measurement points remain stationary during rotation of the outer ring-shaped housing. The signal generation component 645 may be configured as or otherwise support a means for generating one or more electrical signals based at least in part on rotating the outer ring-shaped housing of the wearable ring device, wherein the one or more electrical signals are configured to charge a battery of the wearable ring device, cause a processor of the wearable ring device to perform a ring-inputted command, or both.

Figure 7:
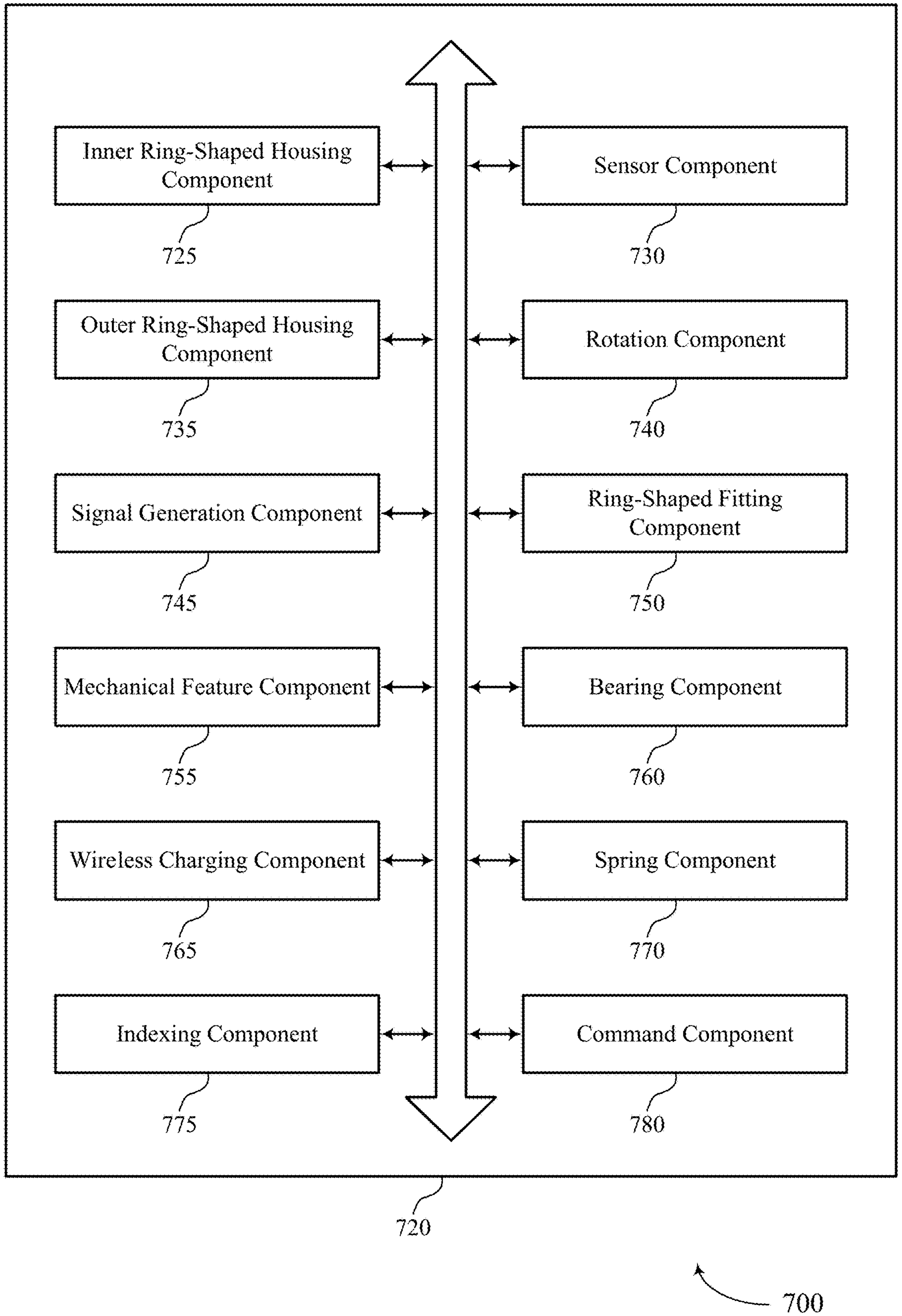
FIG. 7 shows a block diagram of a wearable device manager that supports techniques for manufacturing a wearable ring device with an outer cover capable of rotation in accordance with aspects of the present disclosure.

FIG. 7 shows a block diagram 700 of a wearable device manager 720 that supports techniques for manufacturing a wearable ring device with an outer cover capable of rotation in accordance with aspects of the present disclosure. The wearable device manager 720 may be an example of aspects of a wearable device manager or a wearable device manager 620, or both, as described herein. The wearable device manager 720, or various components thereof, may be an example of means for performing various aspects of techniques for rotating an outer cover of a wearable ring device as described herein. For example, the wearable device manager 720 may include an inner ring-shaped housing component 725, a sensor component 730, an outer ring-shaped housing component 735, a rotation component 740, a signal generation component 745, a ring-shaped fitting component 750, a mechanical feature component 755, a bearing component 760, a wireless charging component 765, a spring component 770, an indexing component 775, a command component 780, or any combination thereof. Each of these components, or components of subcomponents thereof (e.g., one or more processors, one or more memories), may communicate, directly or indirectly, with one another (e.g., via one or more buses).

The inner ring-shaped housing component 725 may be configured as or otherwise support a means for an inner ring-shaped housing comprising one or more apertures, wherein the inner ring-shaped housing defines an inner circumferential surface of the wearable ring device. The sensor component 730 may be configured as or otherwise support a means for one or more sensors disposed at least partially within the inner ring-shaped housing, the one or more sensors configured to acquire physiological data from a user through the one or more apertures, wherein the one or more sensors acquire the physiological data at one or more measurement points at one or more radial positions on a circumference of a finger of the user. The outer ring-shaped housing component 735 may be configured as or otherwise support a means for an outer ring-shaped housing that at least partially surrounds the inner ring-shaped housing, wherein the outer ring-shaped housing defines an outer circumferential surface of the wearable ring device, wherein the outer ring-shaped housing is non-statically coupled with the inner ring-shaped housing such that the outer ring-shaped housing is configured to rotate relative to the inner ring-shaped housing, and wherein the inner ring-shaped housing is configured to remain stationary relative to the finger of the user during rotation of the outer ring-shaped housing such that the one or more measurement points remain unchanged during rotation of the outer ring-shaped housing.

In some examples, the ring-shaped fitting component 750 may be configured as or otherwise support a means for a first ring-shaped fitting that is statically coupled to the inner ring-shaped housing on a first lateral side of the wearable ring device. In some examples, the ring-shaped fitting component 750 may be configured as or otherwise support a means for a second ring-shaped fitting that is statically coupled to the inner ring-shaped housing on a second lateral side of the wearable ring device, wherein the outer ring-shaped housing is non-statically coupled with the first ring-shaped fitting and the second ring-shaped fitting.

In some examples, the mechanical feature component 755 may be configured as or otherwise support a means for a first set of mechanical features within the inner ring-shaped housing. In some examples, the mechanical feature component 755 may be configured as or otherwise support a means for a second set of mechanical features within the outer ring-shaped housing, wherein the second set of mechanical features are configured to non-statically couple to the first set of mechanical features within the inner ring-shaped housing, wherein the outer ring-shaped housing is configured to rotate relative to the inner ring-shaped housing based at least in part on non-statically coupling first set of mechanical features with the second set of mechanical features, wherein the first set of mechanical features comprise a set of grooves, and wherein the second set of mechanical features comprise a set of protrusions, or vice versa.

In some examples, the bearing component 760 may be configured as or otherwise support a means for one or more bearing components positioned between the inner ring-shaped housing and the outer ring-shaped housing, wherein the outer ring-shaped housing is configured to rotate relative to the inner ring-shaped housing based at least in part on the one or more bearing components.

In some examples, the wireless charging component 765 may be configured as or otherwise support a means for one or more wireless charging components positioned at least partially within the inner ring-shaped housing, the outer ring-shaped housing, or both, wherein the wearable ring device is configured to perform an inductive charging procedure to charge a battery positioned within the inner ring-shaped housing based at least in part on the rotation of the outer ring-shaped housing relative to the inner ring-shaped housing.

In some examples, one or more magnets positioned at least partially within the outer ring-shaped housing. In some examples, one or more coils positioned at least partially within the inner ring-shaped housing, wherein rotation of the one or more magnets relative to the one or more coils is configured to induce an electrical current that is used to perform the inductive charging procedure.

In some examples, the wireless charging component 765 may be configured as or otherwise support a means for one or more light emitting devices positioned at least partially within the inner ring-shaped housing, the outer ring-shaped housing, or both, wherein the one or more light emitting devices are configured to emit light while the wearable ring device performs the inductive charging procedure.

In some examples, the spring component 770 may be configured as or otherwise support a means for one or more spring components positioned at least partially within the inner ring-shaped housing, the outer ring-shaped housing, or both, wherein the one or more spring components are configured to return the outer ring-shaped housing to an initial position after rotation.

In some examples, the sensor component 730 may be configured as or otherwise support a means for one or more second sensors disposed at least partially within the inner ring-shaped housing, the one or more second sensors configured to detect a sequence of rotations of the outer ring-shaped housing relative to the inner ring-shaped housing, wherein the wearable ring device is configured to generate a ring-inputted command based at least in part on the sequence of rotations.

In some examples, the indexing component 775 may be configured as or otherwise support a means for one or more indexing components positioned at least partially within the inner ring-shaped housing, the outer ring-shaped housing, or both, wherein the sequence of rotations are detected relative to the one or more indexing components.

In some examples, the ring-inputted command is based at least in part on an index associated with each rotation of the sequence of rotations. In some examples, the index indicates whether the respective rotation is performed clockwise or counterclockwise relative to the one or more indexing components.

In some examples, the ring-inputted command is based at least in part on a radial difference between an end position of the outer ring-shaped housing following each rotation of the sequence of rotations relative to an initial position of the outer ring-shaped housing of the wearable ring device prior to rotation around the inner ring-shaped housing.

In some examples, the ring-inputted command is based at least in part on a rotational magnitude of each rotation of the sequence of rotations relative to an initial position of the outer ring-shaped housing of the wearable ring device prior to rotation around the inner ring-shaped housing.

In some examples, the indexing component 775 may be configured as or otherwise support a means for one or more stopping components positioned at least partially within the inner ring-shaped housing, the outer ring-shaped housing, or both, wherein the one or more stopping components are configured to limit rotation of the outer ring-shaped housing to a radial range, the radial range based at least in part on a position of the one or more stopping components.

Additionally, or alternatively, the wearable device manager 720 may support operating a wearable ring device in accordance with examples as disclosed herein. In some examples, the sensor component 730 may be configured as or otherwise support a means for collecting physiological data associated with a user via one or more sensors of the wearable ring device, wherein the one or more sensors acquire the physiological data at one or more measurement points at one or more radial positions on a circumference of a finger of the user, wherein the wearable ring device comprises an inner ring-shaped housing and an outer ring-shaped housing. The rotation component 740 may be configured as or otherwise support a means for rotating the outer ring-shaped housing of the wearable ring device around the inner ring-shaped housing, wherein the inner ring-shaped housing of the wearable ring device remains stationary during rotation of the outer ring-shaped housing such that the one or more measurement points remain stationary during rotation of the outer ring-shaped housing. The signal generation component 745 may be configured as or otherwise support a means for generating one or more electrical signals based at least in part on rotating the outer ring-shaped housing of the wearable ring device, wherein the one or more electrical signals are configured to charge a battery of the wearable ring device, cause a processor of the wearable ring device to perform a ring-inputted command, or both.

In some examples, the wireless charging component 765 may be configured as or otherwise support a means for performing an inductive charging procedure to charge the battery of the wearable ring device based at least in part on generating the one or more electrical signals.

In some examples, the rotation component 740 may be configured as or otherwise support a means for identifying a sequence of rotations of the outer ring-shaped housing relative to the inner ring-shaped housing. In some examples, the command component 780 may be configured as or otherwise support a means for identifying the ring-inputted command based at least in part on the sequence of rotations. In some examples, the command component 780 may be configured as or otherwise support a means for generating one or more instructions based at least in part on identifying the ring-inputted command, wherein performing the ring-inputted command is based at least in part on generating the one or more instructions.

In some examples, the command component 780 may be configured as or otherwise support a means for identifying an index associated with each rotation of the sequence of rotations based at least in part on one or more indexing components positioned at least partially within the inner ring-shaped housing, the outer ring-shaped housing, or both, wherein the ring-inputted command is based at least in part on the index associated with each rotation of the sequence of rotations.

In some examples, the command component 780 may be configured as or otherwise support a means for identifying an end position of the outer ring-shaped housing following each rotation of the sequence of rotations. In some examples, the command component 780 may be configured as or otherwise support a means for measuring radial differences between the end position of each rotation of the sequence of rotations and an initial position of the outer ring-shaped housing of the wearable ring device prior to rotation around the inner ring-shaped housing, wherein the ring-inputted command is based at least in part on the radial differences.

In some examples, the command component 780 may be configured as or otherwise support a means for identifying a rotational magnitude of each rotation of the sequence of rotations relative to an initial position of the outer ring-shaped housing of the wearable ring device prior to rotation around the inner ring-shaped housing, wherein the ring-inputted command is based at least in part on the rotational magnitude of each rotation of the sequence of rotations.

Figure 8:
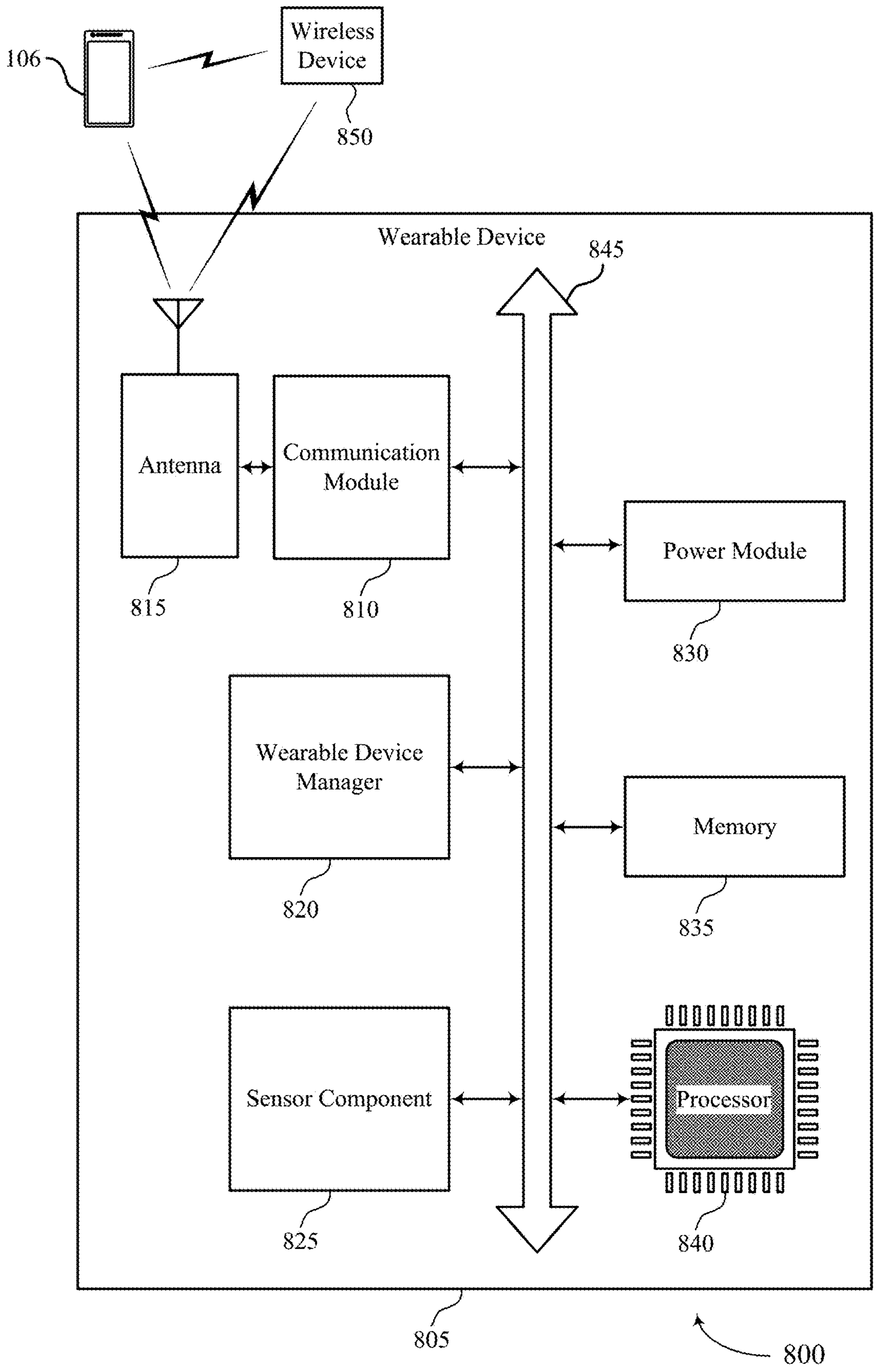
FIG. 8 shows a diagram of a system including a device that supports techniques for manufacturing a wearable ring device with an outer cover capable of rotation in accordance with aspects of the present disclosure.

FIG. 8 shows a diagram of a system 800 including a device 805 that supports techniques for manufacturing a wearable ring device with an outer cover capable of rotation in accordance with aspects of the present disclosure. The device 805 may be an example of or include the components of a device 605 as described herein. The device 805 may include an example of a wearable device 104, as described previously herein. The device 805 may include components for bi-directional communications including components for transmitting and receiving communications with a user device 106 and a server 110, such as a wearable device manager 820, a communication module 810, an antenna 815, a sensor component 825, a power module 830, at least one memory 835, at least one processor 840, and a wireless device 850. These components may be in electronic communication or otherwise coupled (e.g., operatively, communicatively, functionally, electronically, electrically) via one or more buses (e.g., a bus 845).

For example, the wearable device manager 820 may be configured as or otherwise support a means for an inner ring-shaping housing comprising one or more apertures, wherein the inner ring-shaped housing defines an inner circumferential surface of the wearable ring device. The wearable device manager 820 may be configured as or otherwise support a means for one or more sensors disposing at least partially within the inner ring-shaped housing, the one or more sensors configured to acquire physiological data from a user through the one or more apertures, wherein the one or more sensors acquire the physiological data at one or more measurement points at one or more radial positions on a circumference of a finger of the user. The wearable device manager 820 may be configured as or otherwise support a means for an outer ring-shaping housing that at least partially surrounds the inner ring-shaped housing, wherein the outer ring-shaped housing defines an outer circumferential surface of the wearable ring device, wherein the outer ring-shaped housing is non-statically coupled with the inner ring-shaped housing such that the outer ring-shaped housing is configured to rotate relative to the inner ring-shaped housing, and wherein the inner ring-shaped housing is configured to remain stationary relative to the finger of the user during rotation of the outer ring-shaped housing such that the one or more measurement points remain unchanged during rotation of the outer ring-shaped housing.

Additionally, or alternatively, the wearable device manager 820 may support operating a wearable ring device in accordance with examples as disclosed herein. For example, the wearable device manager 820 may be configured as or otherwise support a means for collecting physiological data associated with a user via one or more sensors of the wearable ring device, wherein the one or more sensors acquire the physiological data at one or more measurement points at one or more radial positions on a circumference of a finger of the user, wherein the wearable ring device comprises an inner ring-shaped housing and an outer ring-shaped housing. The wearable device manager 820 may be configured as or otherwise support a means for rotating the outer ring-shaped housing of the wearable ring device around the inner ring-shaped housing, wherein the inner ring-shaped housing of the wearable ring device remains stationary during rotation of the outer ring-shaped housing such that the one or more measurement points remain stationary during rotation of the outer ring-shaped housing. The wearable device manager 820 may be configured as or otherwise support a means for generating one or more electrical signals based at least in part on rotating the outer ring-shaped housing of the wearable ring device, wherein the one or more electrical signals are configured to charge a battery of the wearable ring device, cause a processor of the wearable ring device to perform a ring-inputted command, or both.

Figure 9:
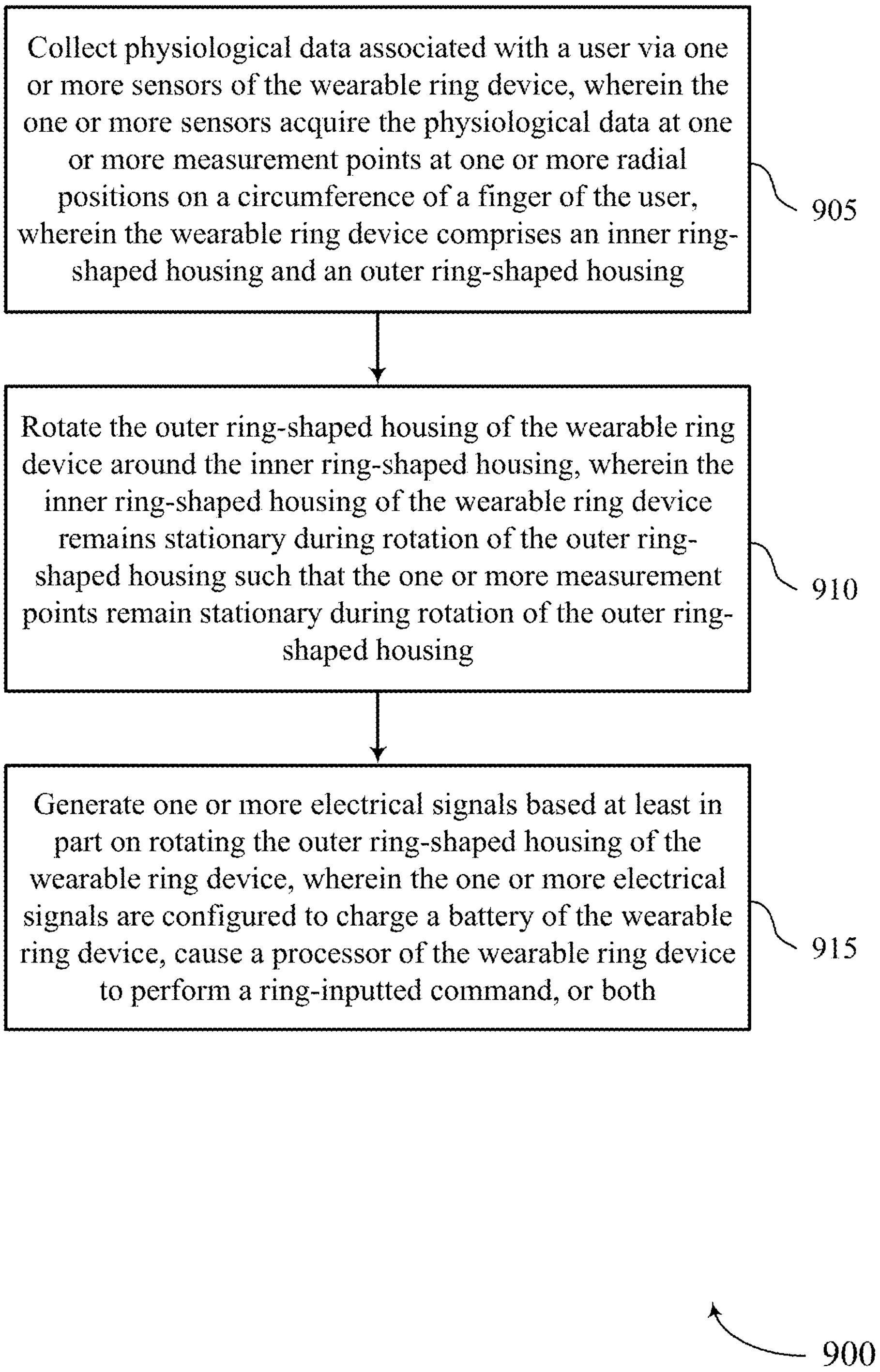
FIGS. 9 through 11 show flowcharts illustrating methods that support techniques for rotating an outer cover of a wearable ring device in accordance with aspects of the present disclosure.

FIG. 9 shows a flowchart illustrating a method 900 that supports techniques for manufacturing a wearable ring device with an outer cover capable of rotation in accordance with aspects of the present disclosure. The operations of the method 900 may be implemented by a wearable device or its components as described herein. For example, the operations of the method 900 may be performed by a wearable device as described with reference to FIGS. 1 through 8. In some examples, a wearable device may execute a set of instructions to control the functional elements of the wearable device to perform the described functions. Additionally, or alternatively, the wearable device may perform aspects of the described functions using special-purpose hardware.

At 905, the method may include collecting physiological data associated with a user via one or more sensors of the wearable ring device, wherein the one or more sensors acquire the physiological data at one or more measurement points at one or more radial positions on a circumference of a finger of the user, wherein the wearable ring device comprises an inner ring-shaped housing and an outer ring-shaped housing. The operations of block 905 may be performed in accordance with examples as disclosed herein. In some examples, aspects of the operations of 905 may be performed by a sensor component 730 as described with reference to FIG. 7.

At 910, the method may include rotating the outer ring-shaped housing of the wearable ring device around the inner ring-shaped housing, wherein the inner ring-shaped housing of the wearable ring device remains stationary during rotation of the outer ring-shaped housing such that the one or more measurement points remain stationary during rotation of the outer ring-shaped housing. The operations of block 910 may be performed in accordance with examples as disclosed herein. In some examples, aspects of the operations of 910 may be performed by a rotation component 740 as described with reference to FIG. 7.

At 915, the method may include generating one or more electrical signals based at least in part on rotating the outer ring-shaped housing of the wearable ring device, wherein the one or more electrical signals are configured to charge a battery of the wearable ring device, cause a processor of the wearable ring device to perform a ring-inputted command, or both. The operations of block 915 may be performed in accordance with examples as disclosed herein. In some examples, aspects of the operations of 915 may be performed by a signal generation component 745 as described with reference to FIG. 7.

Figure 10:
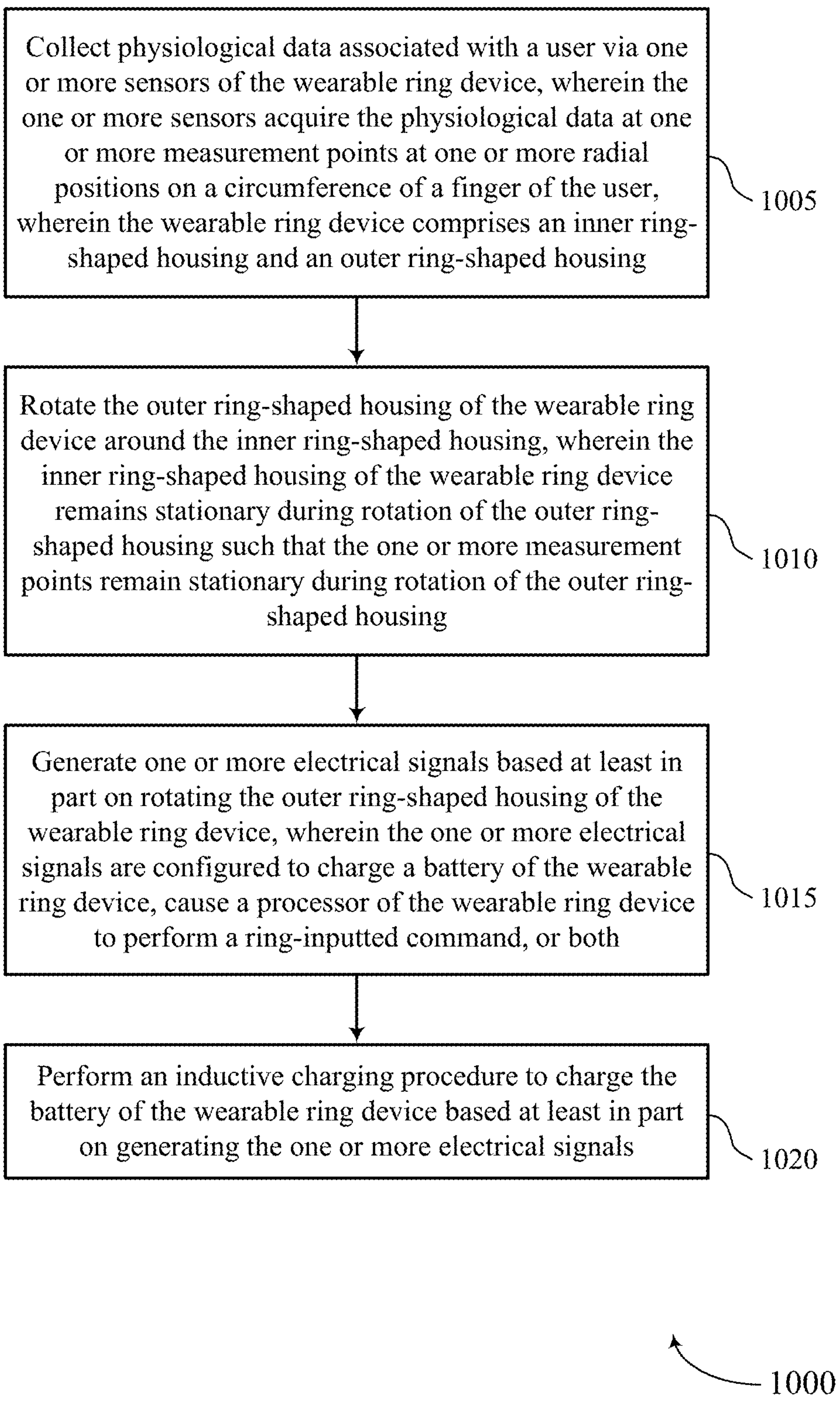

FIG. 10 shows a flowchart illustrating a method 1000 that supports techniques for manufacturing a wearable ring device with an outer cover capable of rotation in accordance with aspects of the present disclosure. The operations of the method 1000 may be implemented by a wearable device or its components as described herein. For example, the operations of the method 1000 may be performed by a wearable device as described with reference to FIGS. 1 through 8. In some examples, a wearable device may execute a set of instructions to control the functional elements of the wearable device to perform the described functions. Additionally, or alternatively, the wearable device may perform aspects of the described functions using special-purpose hardware.

At 1005, the method may include collecting physiological data associated with a user via one or more sensors of the wearable ring device, wherein the one or more sensors acquire the physiological data at one or more measurement points at one or more radial positions on a circumference of a finger of the user, wherein the wearable ring device comprises an inner ring-shaped housing and an outer ring-shaped housing. The operations of block 1005 may be performed in accordance with examples as disclosed herein. In some examples, aspects of the operations of 1005 may be performed by a sensor component 730 as described with reference to FIG. 7.

At 1010, the method may include rotating the outer ring-shaped housing of the wearable ring device around the inner ring-shaped housing, wherein the inner ring-shaped housing of the wearable ring device remains stationary during rotation of the outer ring-shaped housing such that the one or more measurement points remain stationary during rotation of the outer ring-shaped housing. The operations of block 1010 may be performed in accordance with examples as disclosed herein. In some examples, aspects of the operations of 1010 may be performed by a rotation component 740 as described with reference to FIG. 7.

At 1015, the method may include generating one or more electrical signals based at least in part on rotating the outer ring-shaped housing of the wearable ring device, wherein the one or more electrical signals are configured to charge a battery of the wearable ring device, cause a processor of the wearable ring device to perform a ring-inputted command, or both. The operations of block 1015 may be performed in accordance with examples as disclosed herein. In some examples, aspects of the operations of 1015 may be performed by a signal generation component 745 as described with reference to FIG. 7.

At 1020, the method may include performing an inductive charging procedure to charge the battery of the wearable ring device based at least in part on generating the one or more electrical signals. The operations of block 1020 may be performed in accordance with examples as disclosed herein. In some examples, aspects of the operations of 1020 may be performed by a wireless charging component 765 as described with reference to FIG. 7.

Figure 11:
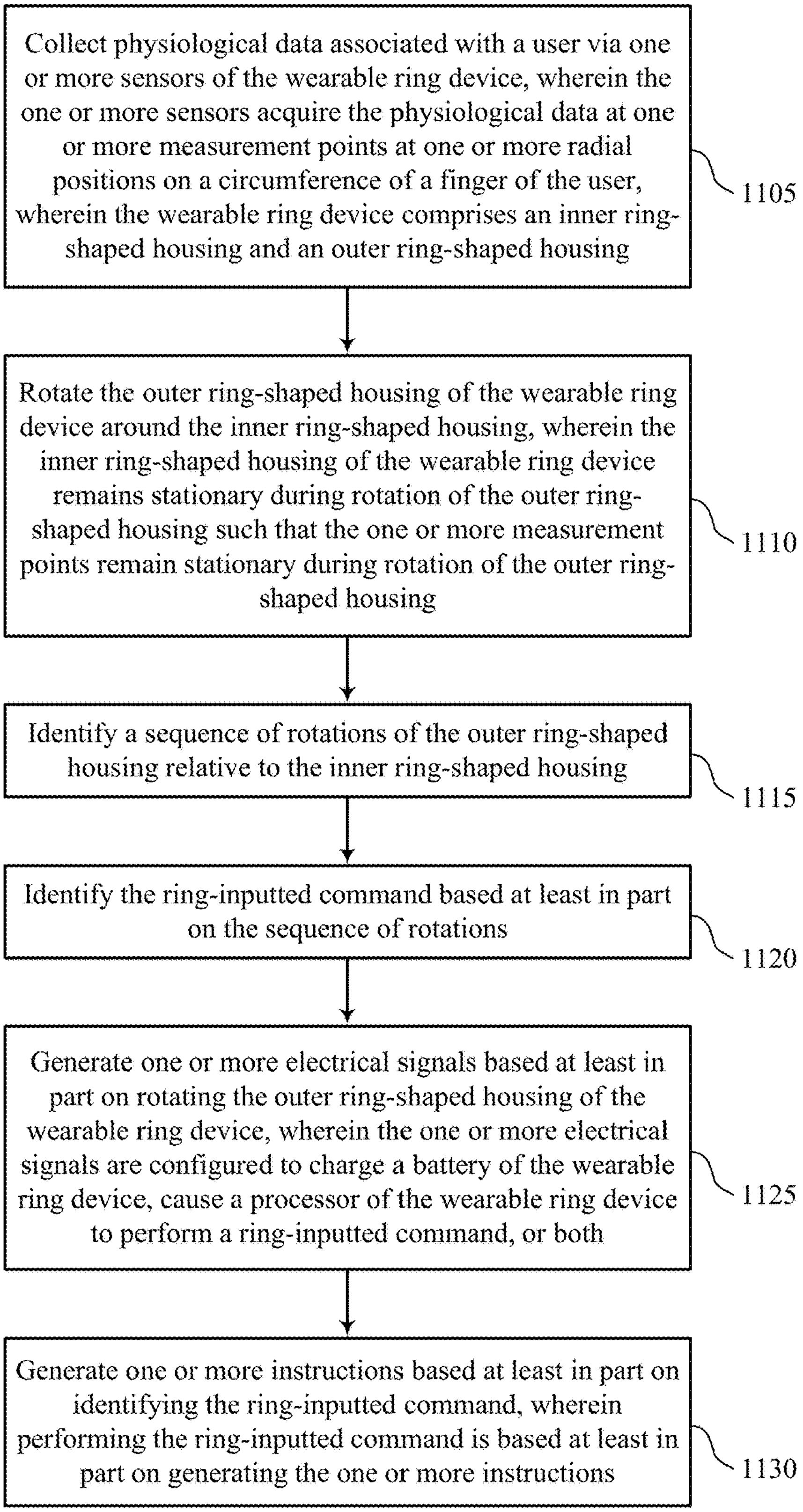

FIG. 11 shows a flowchart illustrating a method 1100 that supports techniques for manufacturing a wearable ring device with an outer cover capable of rotation in accordance with aspects of the present disclosure. The operations of the method 1100 may be implemented by a wearable device or its components as described herein. For example, the operations of the method 1100 may be performed by a wearable device as described with reference to FIGS. 1 through 8. In some examples, a wearable device may execute a set of instructions to control the functional elements of the wearable device to perform the described functions. Additionally, or alternatively, the wearable device may perform aspects of the described functions using special-purpose hardware.

At 1105, the method may include collecting physiological data associated with a user via one or more sensors of the wearable ring device, wherein the one or more sensors acquire the physiological data at one or more measurement points at one or more radial positions on a circumference of a finger of the user, wherein the wearable ring device comprises an inner ring-shaped housing and an outer ring-shaped housing. The operations of block 1105 may be performed in accordance with examples as disclosed herein. In some examples, aspects of the operations of 1105 may be performed by a sensor component 730 as described with reference to FIG. 7.

At 1110, the method may include rotating the outer ring-shaped housing of the wearable ring device around the inner ring-shaped housing, wherein the inner ring-shaped housing of the wearable ring device remains stationary during rotation of the outer ring-shaped housing such that the one or more measurement points remain stationary during rotation of the outer ring-shaped housing. The operations of block 1110 may be performed in accordance with examples as disclosed herein. In some examples, aspects of the operations of 1110 may be performed by a rotation component 740 as described with reference to FIG. 7.

At 1115, the method may include identifying a sequence of rotations of the outer ring-shaped housing relative to the inner ring-shaped housing. The operations of block 1115 may be performed in accordance with examples as disclosed herein. In some examples, aspects of the operations of 1115 may be performed by a rotation component 740 as described with reference to FIG. 7.

At 1120, the method may include identifying the ring-inputted command based at least in part on the sequence of rotations. The operations of block 1120 may be performed in accordance with examples as disclosed herein. In some examples, aspects of the operations of 1120 may be performed by a command component 780 as described with reference to FIG. 7.

At 1125, the method may include generating one or more electrical signals based at least in part on rotating the outer ring-shaped housing of the wearable ring device, wherein the one or more electrical signals are configured to charge a battery of the wearable ring device, cause a processor of the wearable ring device to perform a ring-inputted command, or both. The operations of block 1125 may be performed in accordance with examples as disclosed herein. In some examples, aspects of the operations of 1125 may be performed by a signal generation component 745 as described with reference to FIG. 7.

At 1130, the method may include generating one or more instructions based at least in part on identifying the ring-inputted command, wherein performing the ring-inputted command is based at least in part on generating the one or more instructions. The operations of block 1130 may be performed in accordance with examples as disclosed herein. In some examples, aspects of the operations of 1130 may be performed by a command component 780 as described with reference to FIG. 7.

It should be noted that the methods described above describe possible implementations, and that the operations and the steps may be rearranged or otherwise modified and that other implementations are possible. Furthermore, aspects from two or more of the methods may be combined.

A method by an apparatus is described. The method may include an inner ring-shaped housing comprising one or more apertures, wherein the inner ring-shaped housing defines an inner circumferential surface of the wearable ring device, one or more sensors disposed at least partially within the inner ring-shaped housing, the one or more sensors configured to acquire physiological data from a user through the one or more apertures, wherein the one or more sensors acquire the physiological data at one or more measurement points at one or more radial positions on a circumference of a finger of the user, and an outer ring-shaped housing that at least partially surrounds the inner ring-shaped housing, wherein the outer ring-shaped housing defines an outer circumferential surface of the wearable ring device, wherein the outer ring-shaped housing is non-statically coupled with the inner ring-shaped housing such that the outer ring-shaped housing is configured to rotate relative to the inner ring-shaped housing, and wherein the inner ring-shaped housing is configured to remain stationary relative to the finger of the user during rotation of the outer ring-shaped housing such that the one or more measurement points remain unchanged during rotation of the outer ring-shaped housing.

An apparatus is described. The apparatus may include one or more memories storing processor executable code, and one or more processors coupled with the one or more memories. The one or more processors may individually or collectively operable to execute the code to cause the apparatus to an inner ring-shape housing comprising one or more apertures, wherein the inner ring-shaped housing defines an inner circumferential surface of the wearable ring device, one or more sensors dispose at least partially within the inner ring-shaped housing, the one or more sensors configured to acquire physiological data from a user through the one or more apertures, wherein the one or more sensors acquire the physiological data at one or more measurement points at one or more radial positions on a circumference of a finger of the user, and an outer ring-shape housing that at least partially surrounds the inner ring-shaped housing, wherein the outer ring-shaped housing defines an outer circumferential surface of the wearable ring device, wherein the outer ring-shaped housing is non-statically coupled with the inner ring-shaped housing such that the outer ring-shaped housing is configured to rotate relative to the inner ring-shaped housing, and wherein the inner ring-shaped housing is configured to remain stationary relative to the finger of the user during rotation of the outer ring-shaped housing such that the one or more measurement points remain unchanged during rotation of the outer ring-shaped housing.

Another apparatus is described. The apparatus may include means for an inner ring-shaped housing comprising one or more apertures, wherein the inner ring-shaped housing defines an inner circumferential surface of the wearable ring device, means for one or more sensors disposed at least partially within the inner ring-shaped housing, the one or more sensors configured to acquire physiological data from a user through the one or more apertures, wherein the one or more sensors acquire the physiological data at one or more measurement points at one or more radial positions on a circumference of a finger of the user, and means for an outer ring-shaped housing that at least partially surrounds the inner ring-shaped housing, wherein the outer ring-shaped housing defines an outer circumferential surface of the wearable ring device, wherein the outer ring-shaped housing is non-statically coupled with the inner ring-shaped housing such that the outer ring-shaped housing is configured to rotate relative to the inner ring-shaped housing, and wherein the inner ring-shaped housing is configured to remain stationary relative to the finger of the user during rotation of the outer ring-shaped housing such that the one or more measurement points remain unchanged during rotation of the outer ring-shaped housing.

A non-transitory computer-readable medium storing code is described. The code may include instructions executable by a processor to an inner ring-shape housing comprising one or more apertures, wherein the inner ring-shaped housing defines an inner circumferential surface of the wearable ring device, one or more sensors dispose at least partially within the inner ring-shaped housing, the one or more sensors configured to acquire physiological data from a user through the one or more apertures, wherein the one or more sensors acquire the physiological data at one or more measurement points at one or more radial positions on a circumference of a finger of the user, and an outer ring-shape housing that at least partially surrounds the inner ring-shaped housing, wherein the outer ring-shaped housing defines an outer circumferential surface of the wearable ring device, wherein the outer ring-shaped housing is non-statically coupled with the inner ring-shaped housing such that the outer ring-shaped housing is configured to rotate relative to the inner ring-shaped housing, and wherein the inner ring-shaped housing is configured to remain stationary relative to the finger of the user during rotation of the outer ring-shaped housing such that the one or more measurement points remain unchanged during rotation of the outer ring-shaped housing.

In some examples of the method, apparatus, and non-transitory computer-readable medium described herein, a first ring-shaped fitting that may be statically coupled to the inner ring-shaped housing on a first lateral side of the wearable ring device and a second ring-shaped fitting that may be statically coupled to the inner ring-shaped housing on a second lateral side of the wearable ring device, wherein the outer ring-shaped housing may be non-statically coupled with the first ring-shaped fitting and the second ring-shaped fitting.

In some examples of the method, apparatus, and non-transitory computer-readable medium described herein, a first set of mechanical features within the inner ring-shaped housing and a second set of mechanical features within the outer ring-shaped housing, wherein the second set of mechanical features may be configured to non-statically couple to the first set of mechanical features within the inner ring-shaped housing, wherein the outer ring-shaped housing may be configured to rotate relative to the inner ring-shaped housing based at least in part on non-statically coupling first set of mechanical features with the second set of mechanical features, wherein the first set of mechanical features comprise a set of grooves, and wherein the second set of mechanical features comprise a set of protrusions, or vice versa.

In some examples of the method, apparatus, and non-transitory computer-readable medium described herein, one or more bearing components positioned between the inner ring-shaped housing and the outer ring-shaped housing, wherein the outer ring-shaped housing may be configured to rotate relative to the inner ring-shaped housing based at least in part on the one or more bearing components.

In some examples of the method, apparatus, and non-transitory computer-readable medium described herein, one or more wireless charging components positioned at least partially within the inner ring-shaped housing, the outer ring-shaped housing, or both, wherein the wearable ring device may be configured to perform an inductive charging procedure to charge a battery positioned within the inner ring-shaped housing based at least in part on the rotation of the outer ring-shaped housing relative to the inner ring-shaped housing.

In some examples of the method, apparatus, and non-transitory computer-readable medium described herein, one or more magnets positioned at least partially within the outer ring-shaped housing and one or more coils positioned at least partially within the inner ring-shaped housing, wherein rotation of the one or more magnets relative to the one or more coils may be configured to induce an electrical current that may be used to perform the inductive charging procedure.

In some examples of the method, apparatus, and non-transitory computer-readable medium described herein, one or more light emitting devices positioned at least partially within the inner ring-shaped housing, the outer ring-shaped housing, or both, wherein the one or more light emitting devices may be configured to emit light while the wearable ring device performs the inductive charging procedure.

In some examples of the method, apparatus, and non-transitory computer-readable medium described herein, one or more spring components positioned at least partially within the inner ring-shaped housing, the outer ring-shaped housing, or both, wherein the one or more spring components may be configured to return the outer ring-shaped housing to an initial position after rotation.

In some examples of the method, apparatus, and non-transitory computer-readable medium described herein, one or more second sensors disposed at least partially within the inner ring-shaped housing, the one or more second sensors configured to detect a sequence of rotations of the outer ring-shaped housing relative to the inner ring-shaped housing, wherein the wearable ring device may be configured to generate a ring-inputted command based at least in part on the sequence of rotations.

In some examples of the method, apparatus, and non-transitory computer-readable medium described herein, one or more indexing components positioned at least partially within the inner ring-shaped housing, the outer ring-shaped housing, or both, wherein the sequence of rotations may be detected relative to the one or more indexing components.

In some examples of the method, apparatus, and non-transitory computer-readable medium described herein, the ring-inputted command may be based at least in part on an index associated with each rotation of the sequence of rotations and the index indicates whether the respective rotation may be performed clockwise or counterclockwise relative to the one or more indexing components.

In some examples of the method, apparatus, and non-transitory computer-readable medium described herein, the ring-inputted command may be based at least in part on a radial difference between an end position of the outer ring-shaped housing following each rotation of the sequence of rotations relative to an initial position of the outer ring-shaped housing of the wearable ring device prior to rotation around the inner ring-shaped housing.

In some examples of the method, apparatus, and non-transitory computer-readable medium described herein, the ring-inputted command may be based at least in part on a rotational magnitude of each rotation of the sequence of rotations relative to an initial position of the outer ring-shaped housing of the wearable ring device prior to rotation around the inner ring-shaped housing.

In some examples of the method, apparatus, and non-transitory computer-readable medium described herein, one or more stopping components positioned at least partially within the inner ring-shaped housing, the outer ring-shaped housing, or both, wherein the one or more stopping components may be configured to limit rotation of the outer ring-shaped housing to a radial range, the radial range based at least in part on a position of the one or more stopping components.

A method for operating a wearable ring device by an apparatus is described. The method may include collecting physiological data associated with a user via one or more sensors of the wearable ring device, wherein the one or more sensors acquire the physiological data at one or more measurement points at one or more radial positions on a circumference of a finger of the user, wherein the wearable ring device comprises an inner ring-shaped housing and an outer ring-shaped housing, rotating the outer ring-shaped housing of the wearable ring device around the inner ring-shaped housing, wherein the inner ring-shaped housing of the wearable ring device remains stationary during rotation of the outer ring-shaped housing such that the one or more measurement points remain stationary during rotation of the outer ring-shaped housing, and generating one or more electrical signals based at least in part on rotating the outer ring-shaped housing of the wearable ring device, wherein the one or more electrical signals are configured to charge a battery of the wearable ring device, cause a processor of the wearable ring device to perform a ring-inputted command, or both.

An apparatus for operating a wearable ring device is described. The apparatus may include one or more memories storing processor executable code, and one or more processors coupled with the one or more memories. The one or more processors may individually or collectively operable to execute the code to cause the apparatus to collect physiological data associated with a user via one or more sensors of the wearable ring device, wherein the one or more sensors acquire the physiological data at one or more measurement points at one or more radial positions on a circumference of a finger of the user, wherein the wearable ring device comprises an inner ring-shaped housing and an outer ring-shaped housing, rotate the outer ring-shaped housing of the wearable ring device around the inner ring-shaped housing, wherein the inner ring-shaped housing of the wearable ring device remains stationary during rotation of the outer ring-shaped housing such that the one or more measurement points remain stationary during rotation of the outer ring-shaped housing, and generate one or more electrical signals based at least in part on rotating the outer ring-shaped housing of the wearable ring device, wherein the one or more electrical signals are configured to charge a battery of the wearable ring device, cause a processor of the wearable ring device to perform a ring-inputted command, or both.

Another apparatus for operating a wearable ring device is described. The apparatus may include means for collecting physiological data associated with a user via one or more sensors of the wearable ring device, wherein the one or more sensors acquire the physiological data at one or more measurement points at one or more radial positions on a circumference of a finger of the user, wherein the wearable ring device comprises an inner ring-shaped housing and an outer ring-shaped housing, means for rotating the outer ring-shaped housing of the wearable ring device around the inner ring-shaped housing, wherein the inner ring-shaped housing of the wearable ring device remains stationary during rotation of the outer ring-shaped housing such that the one or more measurement points remain stationary during rotation of the outer ring-shaped housing, and means for generating one or more electrical signals based at least in part on rotating the outer ring-shaped housing of the wearable ring device, wherein the one or more electrical signals are configured to charge a battery of the wearable ring device, cause a processor of the wearable ring device to perform a ring-inputted command, or both.

A non-transitory computer-readable medium storing code for operating a wearable ring device is described. The code may include instructions executable by a processor to collect physiological data associated with a user via one or more sensors of the wearable ring device, wherein the one or more sensors acquire the physiological data at one or more measurement points at one or more radial positions on a circumference of a finger of the user, wherein the wearable ring device comprises an inner ring-shaped housing and an outer ring-shaped housing, rotate the outer ring-shaped housing of the wearable ring device around the inner ring-shaped housing, wherein the inner ring-shaped housing of the wearable ring device remains stationary during rotation of the outer ring-shaped housing such that the one or more measurement points remain stationary during rotation of the outer ring-shaped housing, and generate one or more electrical signals based at least in part on rotating the outer ring-shaped housing of the wearable ring device, wherein the one or more electrical signals are configured to charge a battery of the wearable ring device, cause a processor of the wearable ring device to perform a ring-inputted command, or both.

Some examples of the method, apparatus, and non-transitory computer-readable medium described herein may further include operations, features, means, or instructions for performing an inductive charging procedure to charge the battery of the wearable ring device based at least in part on generating the one or more electrical signals.

Some examples of the method, apparatus, and non-transitory computer-readable medium described herein may further include operations, features, means, or instructions for identifying a sequence of rotations of the outer ring-shaped housing relative to the inner ring-shaped housing, identifying the ring-inputted command based at least in part on the sequence of rotations, and generating one or more instructions based at least in part on identifying the ring-inputted command, wherein performing the ring-inputted command may be based at least in part on generating the one or more instructions.

Some examples of the method, apparatus, and non-transitory computer-readable medium described herein may further include operations, features, means, or instructions for identifying an index associated with each rotation of the sequence of rotations based at least in part on one or more indexing components positioned at least partially within the inner ring-shaped housing, the outer ring-shaped housing, or both, wherein the ring-inputted command may be based at least in part on the index associated with each rotation of the sequence of rotations.

Some examples of the method, apparatus, and non-transitory computer-readable medium described herein may further include operations, features, means, or instructions for identifying an end position of the outer ring-shaped housing following each rotation of the sequence of rotations and measuring radial differences between the end position of each rotation of the sequence of rotations and an initial position of the outer ring-shaped housing of the wearable ring device prior to rotation around the inner ring-shaped housing, wherein the ring-inputted command may be based at least in part on the radial differences.

Some examples of the method, apparatus, and non-transitory computer-readable medium described herein may further include operations, features, means, or instructions for identifying a rotational magnitude of each rotation of the sequence of rotations relative to an initial position of the outer ring-shaped housing of the wearable ring device prior to rotation around the inner ring-shaped housing, wherein the ring-inputted command may be based at least in part on the rotational magnitude of each rotation of the sequence of rotations.

The description set forth herein, in connection with the appended drawings, describes example configurations and does not represent all the examples that may be implemented or that are within the scope of the claims. The term "exemplary" used herein means "serving as an example, instance, or illustration," and not "preferred" or "advantageous over other examples." The detailed description includes specific details for the purpose of providing an understanding of the described techniques. These techniques, however, may be practiced without these specific details. In some instances, well-known structures and devices are shown in block diagram form in order to avoid obscuring the concepts of the described examples.

In the appended figures, similar components or features may have the same reference label. Further, various components of the same type may be distinguished by following the reference label by a dash and a second label that distinguishes among the similar components. If just the first reference label is used in the specification, the description is applicable to any one of the similar components having the same first reference label irrespective of the second reference label.

Information and signals described herein may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, or any combination thereof.

The various illustrative blocks and modules described in connection with the disclosure herein may be implemented or performed with a general-purpose processor, a DSP, an ASIC, an FPGA or other programmable logic device, discrete gate or transistor logic, discrete hardware components, or any combination thereof designed to perform the functions described herein. A general-purpose processor may be a microprocessor, but in the alternative, the processor may be any conventional processor, controller, microcontroller, or state machine. A processor may also be implemented as a combination of computing devices (e.g., a combination of a DSP and a microprocessor, multiple microprocessors, one or more microprocessors in conjunction with a DSP core, or any other such configuration).

The functions described herein may be implemented in hardware, software executed by a processor, firmware, or any combination thereof. If implemented in software executed by a processor, the functions may be stored on or transmitted over as one or more instructions or code on a computer-readable medium. Other examples and implementations are within the scope of the disclosure and appended claims. For example, due to the nature of software, functions described above can be implemented using software executed by a processor, hardware, firmware, hardwiring, or combinations of any of these. Features implementing functions may also be physically located at various positions, including being distributed such that portions of functions are implemented at different physical locations. Also, as used herein, including in the claims, "or" as used in a list of items (for example, a list of items prefaced by a phrase such as "at least one of" or "one or more of") indicates an inclusive list such that, for example, a list of at least one of A, B, or C means A or B or C or AB or AC or BC or ABC (i.e., A and B and C). Also, as used herein, the phrase "based on" shall not be construed as a reference to a closed set of conditions. For example, an exemplary step that is described as "based on condition A" may be based on both a condition A and a condition B without departing from the scope of the present disclosure. In other words, as used herein, the phrase "based on" shall be construed in the same manner as the phrase "based at least in part on."

Computer-readable media includes both non-transitory computer storage media and communication media including any medium that facilitates transfer of a computer program from one place to another. A non-transitory storage medium may be any available medium that can be accessed by a general purpose or special purpose computer. By way of example, and not limitation, non-transitory computer-readable media can comprise RAM, ROM, electrically erasable programmable ROM (EEPROM), compact disk (CD) ROM or other optical disk storage, magnetic disk storage or other magnetic storage devices, or any other non-transitory medium that can be used to carry or store desired program code means in the form of instructions or data structures and that can be accessed by a general-purpose or special-purpose computer, or a general-purpose or special-purpose processor. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, include CD, laser disc, optical disc, digital versatile disc (DVD), floppy disk and Blu-ray disc where disks usually reproduce data magnetically, while discs reproduce data optically with lasers. Combinations of the above are also included within the scope of computer-readable media.

The description herein is provided to enable a person skilled in the art to make or use the disclosure. Various modifications to the disclosure will be readily apparent to those skilled in the art, and the generic principles defined herein may be applied to other variations without departing from the scope of the disclosure. Thus, the disclosure is not limited to the examples and designs described herein, but is to be accorded the broadest scope consistent with the principles and novel features disclosed herein.

What is claimed is:

1. A wearable ring device, comprising:

an inner ring-shaped housing comprising one or more apertures, wherein the inner ring-shaped housing defines an inner curved surface of the wearable ring device; one or more sensors disposed at least partially within the inner ring-shaped housing, the one or more sensors configured to sense physiological signals from a user through the one or more apertures, wherein the one or more sensors acquire the physiological data at one or more measurement points at one or more radial positions on a finger of the user;

a first side cover that is statically coupled to the inner ring-shaped housing on a first lateral side of the wearable ring device;

a second side cover that is statically coupled to the inner ring-shaped housing on a second lateral side of the wearable ring device; and an outer ring-shaped housing that at least partially surrounds the inner ring-shaped housing, wherein the outer ring-shaped housing defines an outer curved surface of the wearable ring device, wherein the outer ring-shaped housing is non-statically coupled with the first side cover on the first lateral side of the wearable ring device and the second side cover on the second lateral side of the wearable ring device, such that the outer ring-shaped housing is configured to rotate relative to the inner ring-shaped housing, and wherein the inner ring-shaped housing is configured to remain stationary relative to the finger of the user during rotation of the outer ring-shaped housing such that the one or more measurement points remain unchanged during rotation of the outer ring-shaped housing.

2. The wearable ring device of claim 1, further comprising:

a first set of mechanical features within the inner ring-shaped housing; and a second set of mechanical features within the outer ring-shaped housing, wherein the second set of mechanical features are configured to non-statically couple to the first set of mechanical features within the inner ring-shaped housing, wherein the outer ring-shaped housing is configured to rotate relative to the inner ring-shaped housing based at least in part on non-statically coupling the first set of mechanical features with the second set of mechanical features, wherein the first set of mechanical features comprise a set of grooves, and wherein the second set of mechanical features comprise a set of protrusions, or vice versa.

3. The wearable ring device of claim 1, further comprising:

one or more bearing components positioned between the inner ring-shaped housing and the outer ring-shaped housing, wherein the outer ring-shaped housing is configured to rotate relative to the inner ring-shaped housing based at least in part on the one or more bearing components.

4. The wearable ring device of claim 1, further comprising: one or more wireless charging components positioned at least partially within the inner ring-shaped housing, the outer ring-shaped housing, or both, wherein the wearable ring device is configured to perform an inductive charging procedure to charge a battery positioned within the inner ring-shaped housing based at least in part on the rotation of the outer ring-shaped housing relative to the inner ring-shaped housing.

5. The wearable ring device of claim 4, wherein the one or more wireless charging components comprise:

one or more magnets positioned at least partially within the outer ring-shaped housing; and one or more coils positioned at least partially within the inner ring-shaped housing, wherein rotation of the one or more magnets relative to the one or more coils is configured to induce an electrical current that is used to perform the inductive charging procedure.

6. The wearable ring device of claim 4, further comprising:

one or more light emitting devices positioned at least partially within the inner ring-shaped housing, the outer ring-shaped housing, or both, wherein the one or more light emitting devices are configured to emit light while the wearable ring device performs the inductive charging procedure.

7. The wearable ring device of claim 1, further comprising:

one or more spring components positioned at least partially within the inner ring-shaped housing, the outer ring-shaped housing, or both, wherein the one or more spring components are configured to return the outer ring-shaped housing to an initial position after rotation.

8. The wearable ring device of claim 1, further comprising:

one or more second sensors disposed at least partially within the inner ring-shaped housing, the one or more second sensors configured to detect a sequence of rotations of the outer ring-shaped housing relative to the inner ring-shaped housing, wherein the wearable ring device is configured to generate a ring-inputted command based at least in part on the sequence of rotations.

9. The wearable ring device of claim 8, further comprising:

one or more indexing components positioned at least partially within the inner ring-shaped housing, the outer ring-shaped housing, or both, wherein the sequence of rotations are detected relative to the one or more indexing components.

10. The wearable ring device of claim 9, wherein the ring-inputted command is based at least in part on an index associated with each rotation of the sequence of rotations, and wherein the index indicates whether the respective rotation is performed clockwise or counterclockwise relative to the one or more indexing components.

11. The wearable ring device of claim 8, wherein the ring-inputted command is based at least in part on a radial difference between an end position of the outer ring-shaped housing following each rotation of the sequence of rotations relative to an initial position of the outer ring-shaped housing of the wearable ring device prior to rotation around the inner ring-shaped housing.

12. The wearable ring device of claim 8, wherein the ring-inputted command is based at least in part on a rotational magnitude of each rotation of the sequence of rotations relative to an initial position of the outer ring-shaped housing of the wearable ring device prior to rotation around the inner ring-shaped housing.

13. The wearable ring device of claim 1, further comprising: one or more stopping components positioned at least partially within the inner ring-shaped housing, the outer ring-shaped housing, or both, wherein the one or more stopping components are configured to limit rotation of the outer ring-shaped housing to a radial range, the radial range based at least in part on a position of the one or more stopping components.

* * * * *